(12) United States Patent
Ndam et al.

(10) Patent No.: US 9,855,321 B2
(45) Date of Patent: Jan. 2, 2018

(54) VACCINES AGAINST PREGNANCY-ASSOCIATED MALARIA

(71) Applicant: INSTITUT DE RECHERCHE POUR LE DÉVELOPPEMENT (IRD), Marseilles (FR)

(72) Inventors: Nicaise Tuikue Ndam, Paris (FR); Philippe Deloron, Paris (FR); Justin Doritchamou, Paris (FR)

(73) Assignee: INSTITUT DE RECHERCHE POUR LE DÉVELOPPEMENT (IRD), Marseilles (FR)

( * ) Notice: Subject to any disclaimer, the term of this patent is extended or adjusted under 35 U.S.C. 154(b) by 0 days.

(21) Appl. No.: 14/762,300

(22) PCT Filed: Jan. 21, 2014

(86) PCT No.: PCT/EP2014/051149
§ 371 (c)(1),
(2) Date: Jul. 21, 2015

(87) PCT Pub. No.: WO2014/111597
PCT Pub. Date: Jul. 24, 2014

(65) Prior Publication Data
US 2016/0136253 A1    May 19, 2016

(30) Foreign Application Priority Data
Jan. 21, 2013  (FR) ..................... 13 50508

(51) Int. Cl.
*A61K 39/015* (2006.01)
*A61K 39/00* (2006.01)
*C07K 14/445* (2006.01)

(52) U.S. Cl.
CPC ........ *A61K 39/015* (2013.01); *A61K 2039/53* (2013.01)

(58) Field of Classification Search
CPC ...... A61K 39/015; A61K 39/00; A61K 38/00; A61K 39/38; C07K 14/445; C07K 14/00; C07K 17/00; C07H 21/02
See application file for complete search history.

(56) References Cited

FOREIGN PATENT DOCUMENTS

WO    WO-2012/014073 A2    2/2012

OTHER PUBLICATIONS

Bordbar et al., (Vaccine. 2012. vol. 30. No. 7: 1343-1348).*
International Search Report issued in PCT/EP2014/051149 dated Apr. 15, 2014.

(Continued)

*Primary Examiner* — Ja'Na Hines
(74) *Attorney, Agent, or Firm* — Marshall, Gerstein & Borun LLP

(57) ABSTRACT

The present invention relates to combinations of polypeptides or of polynucleotides corresponding to a specific region of the N-terminal portion of the VAR2CSA protein of different parasitic families or lines of *Plasmodium falciparum*, and to their use in the prevention of pregnancy-associated malaria. The invention also relates to immunogenic compositions and to vaccines useful for preventing malaria in pregnant women.

11 Claims, 5 Drawing Sheets

(56) References Cited

OTHER PUBLICATIONS

Figure 1:
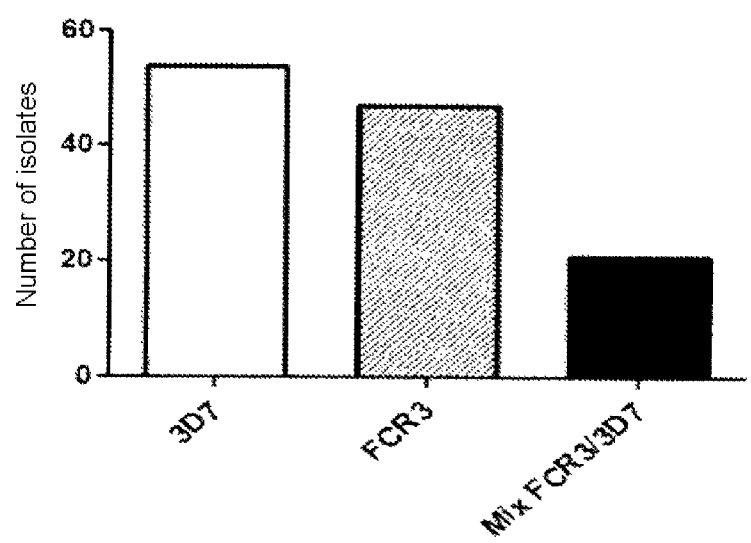

Bordbar et al., "Identification of ld1-DBL2X of VAR2CSA as a Key Domain Inducing Highly Inhibitory and Cross-Reactive Antibodies," Vaccine, vol. 30, No. 7, Feb. 1, 2012, pp. 1343-1348.

Sander et al., "Multiple var2csa-Type PfEMP1 Genes Located at Different Chromosomal Loci Occur in Many Plasmodium falciparum Isolates," PLOS ONE, vol. 4, No. 8, Aug. 2009.

Nielsen et al., "Plasmodium falciparum: VAR2CSA expressed during pregnancy-associated malaria is partially resistant toproteolytic cleavage by trypsin," Experimental Parasitology, vol. 117, No. 1, Sep. 2007.

\* cited by examiner

VACCINES AGAINST PREGNANCY-ASSOCIATED MALARIA

RELATED PATENT APPLICATIONS

The present application is filed pursuant to 35 U.S.C. §371 as a U.S. National Phase Application of International Patent Application No. PCT/EP2014/051149, which was filed on Jan. 21, 2014, claiming the benefit of priority to French application number FR 13 50508 filed on 21 Jan. 2013. The content of each of the aforementioned patent applications is incorporated here by reference in its entirety.

FIELD OF THE INVENTION

The present invention relates to the use of combinations of specific regions of the N-terminal portion of the VAR2CSA protein derived from various parasitic families or lines of *Plasmodium falciparum* in the prevention and/or treatment of pregnancy-associated malaria.

Context of the invention Malaria (paludism) is the commonest of the parasitic infections observed in the world. It is due to a parasite of the genus *Plasmodium*, which is transmitted by the bite of a female mosquito (*Anopheles*). Several *Plasmodium* species can infect humans, but *Plasmodium falciparum* is the commonest and most pathogenic species and the one that is responsible for fatal cases. Once introduced into the blood, the parasite infects the liver cells, in which it proliferates, before circulating in the blood again and invading the red blood cells (erythrocytes). Malaria affects about a hundred countries in the world, particularly in the disadvantaged tropical zones of Africa, Asia and Latin America; Africa being the continent most affected by far. According to the estimates of the World Health Organization, malaria is responsible annually for 225 million cases of fever and about 1 million deaths (World Malaria Report, WHO, 2010). Existing means for combating it are antimalarials (the best known being chloroquine and quinine) and tackling the mosquitoes that are the vectors of the parasite. However, the situation is more worrying than some years ago; the parasites are becoming more and more resistant to the medications and the mosquitoes are developing resistance to insecticides. No vaccine is available at present.

Malaria mainly affects children under 5 years of age and pregnant women, in particular primigravidae (i.e. women pregnant for the first time). Pregnant women are particularly vulnerable as the placenta constitutes a target where the parasites may accumulate. In pregnant women, malarial infection may cause a whole range of detrimental effects: spontaneous abortion, premature birth, inadequate birth weight, congenital transmission, and neonatal death. In zones of Africa where malaria is endemic, 3 to 5% of the deaths of children at birth may be ascribed to pregnancy-associated malaria. Moreover, it also presents a real danger for the mother, who may suffer anemia, which is sometimes severe, or even fatal.

Currently, prevention of malaria in pregnant women is based on prophylactic treatment with sulfadoxine-pyrimethamine (Cot et al., Br. Med. Bull., 2003, 67: 137-148). However, this intermittent treatment is not able to provide prevention of malaria throughout pregnancy: firstly, because the drug is only administered starting from the 20th week of pregnancy (as the teratogenic risk during embryogenesis is considered too great); secondly, because it is based on two administrations of sulfadoxine-pyrimethamine at therapeutic dose at least one month apart, which only provides partial medicinal protection; and thirdly, because the efficacy of sulfadoxine-pyrimethamine is now decreasing considerably in all malaria-endemic regions owing to expansion of parasitic resistance (Cot et al., Am. J. Trop. Med. Hyg., 1998, 59: 813-822; WHO/HTM/MAL/2005.1103. Geneva: World Health Organization; ter Kuile et al., JAMA, 2007, 297: 2603-2616; Mockenhaupt et al., J. Infect. Dis., 2008, 198: 1545-1549; Briand et al., J. Infect. Dis., 2009, 991-1001; Harrington et al., Proc. Natl. Acad. Sci. USA, 2009, 106: 9027-9032). Medicinal products are currently under investigation in this context, and much effort is also focused on development of a vaccine against pregnancy-associated malaria. The possibility of vaccinating pregnant women or prepubescent girls would constitute an obvious advantage over drug treatment, in that preventive cover of pregnancy would be extended, and would potentially be of better quality.

One of the vaccine strategies envisaged for combating pregnancy-associated malaria is to recreate natural protective immunity. In fact, the clinical severity of malaria due to *Plasmodium falciparum* is partly connected with changes of the infected erythrocytes. These changes are induced by the proteins of the parasite, which are exported to the surface of the erythrocytes during the development stage in the blood. Certain of these surface proteins of the PfEMP1 family (*Plasmodium falciparum* Erythrocyte Membrane Protein 1), encoded by the parasites, confer new cytoadherence properties on the erythrocytes. The erythrocytes are then capable of adhering to the inside wall of blood vessels, thereby preventing transport of the infected erythrocytes to the purifying organs of the immune system, one of the roles of which is to destroy cells recognized as abnormal. In the case of pregnancy-associated malaria, the parasitized erythrocytes adhere to a sugar, chondroitin sulfate A (CSA), present in the placenta. After several pregnancies, women acquire protective antibodies that block this adhesion. One vaccine strategy is to recreate this protective immunity, by blocking adhesion of the infected erythrocytes to the placenta.

The VAR2CSA protein, one of the proteins of the PfEMP1 family, is currently the subject of many investigations with a view to obtaining a specific vaccine for pregnant women (Tuikue Ndam et al., J. Infect. Dis., 2005, 192: 331-335; Chia et al., J. Infect. Dis., 2005, 192: 1284-1293; Tuikue Ndam et al., J. Infect. Dis., 2006, 193: 713-720; Dahlback et al., PLoS Pathogens, 2006, 2: 1069-1082; Badaut et al., Mol. Biochem. Parasitol., 2007, 15: 89-99; Khattab et al., Parasitol. Res., 2007, 101: 767-774; Guitard et al., Malaria J., 2008, 11:7-10; Guitard et al., Malaria J., 2010, 9: 165; Gaignard et al., Mol. Biochem. Parasitol., 2010, 173: 115-122; Gnidehou et al., Mol. Biochem. Parasitol., 2010, 5(10): e13105; WO 2012/014073). These works come up against polymorphism of VAR2CSA, but phase 1 studies are nevertheless envisaged. The whole of the extracellular domain of this protein has been expressed in a heterologous system (Srivastava et al., Proc. Natl. Acad. Sci. USA, 2010, 107: 4884-4889; Khunrae et al., J. Mol. Biol., 2010, 397: 826-834), and the antibodies induced against this extracellular domain display a very high level of antiadherence. However, development of new vaccine approaches will have to take into account the numerous immunodominant epitopes that do not induce "antiadherence" antibodies.

It therefore appears crucial to continue to explore and develop new strategies for combating and preventing pregnancy-associated malaria.

SUMMARY OF THE INVENTION

The present inventors have previously identified the N-terminal region of VAR2CSA, and notably the NTS- DBL1x-Id1-DBL2x region consisting of the DBL1x domain, the Id1 interdomain and the DBL2x domain, as being the region that contains epitopes capable of inducing, in vivo, antibodies that block adherence of erythrocytes infected by *Plasmodium falciparum* to CSA, and the Id1-DBL2x subregion as being the minimal antigenic region of VAR2CSA involved in the acquisition of protective immunity with respect to the placental sequestration that occurs in pregnancy-associated malaria (WO 2012/014073). They have now discovered that the combination of antibodies induced against the NTS-DBL1x-Id1-DBL2x region of VAR2CSA of the two parasite lines FCR3 and 3D7 of *Plasmodium falciparum* completely inhibit fixation of the parasitized erythrocytes to chondroitin sulfate A (CSA) both on placental field isolates from pregnant women and on well-characterized laboratory strains. For comparison, the antibodies induced against the NTS-DBL1x-Id1-DBL2x region of VAR2CSA of each of the two parasite lines FCR3 and 3D7 of *Plasmodium falciparum* used separately only display a percentage inhibition of about 70%. By analyzing the sequences of parasitic isolates from pregnant women in Benin, the inventors also demonstrated segregation of the parasitic variants in the Id1 interdomain of VAR2CSA. This new dichotomy domain has never been described previously. Sequence alignments led to the establishment of two consensus sequences representative of the Id1 interdomain of VAR2CSA: the first Id1A (or SEQ ID NO: 11) corresponds to a recently identified cluster, and the second Id1B (or SEQ ID NO: 12) corresponds to the other group of sequences (of which the line FCR3 and the line 3D7 form part).

Accordingly, a first aspect of the present invention relates to the use of combinations of polypeptide or polynucleotide sequences corresponding to the NTS-DBL1x-Id1-DBL2x region or to the Id1-DBL2x region of the VAR2CSA protein derived from different parasitic families of *Plasmodium falciparum*, in the management of malaria in pregnant women.

More specifically, the present invention relates to the use of isolated or purified polypeptide or polynucleotide sequences corresponding to the NTS-DBL1x-Id1-DBL2x region or to the Id1-DBL2x region of the VAR2CSA protein derived from *Plasmodium falciparum* parasites whose VAR2CSA protein is characterized by an Id1 interdomain having as sequence the consensus sequence SEQ ID NO: 11 (or that is encoded by the consensus nucleic acid sequence SEQ ID NO: 13) and optionally from polypeptide or polynucleotide sequences corresponding to the NTS-DBL1x-Id1-DBL2x region or to the Id1-DBL2x region of the VAR2CSA protein derived from *Plasmodium falciparum* parasites whose VAR2CSA protein is characterized by an Id1 interdomain that has as sequence the consensus sequence SEQ ID NO: 12 (or that is encoded by the consensus nucleic acid sequence SEQ ID NO: 14).

In particular, the present invention relates to a combination of at least two isolated or purified polypeptides for use in the treatment or prevention of pregnancy-associated malaria, the first isolated or purified polypeptide consisting of the NTS-DBL1x-Id1-DBL2x region or the Id1-DBL2x region of the VAR2CSA protein of a first parasitic family of *Plasmodium falciparum*, and the second isolated or purified polypeptide consisting of the NTS-DBL1x-Id1-DBL2x region or the Id1-DBL2x region of the VAR2CSA protein of a second parasitic family of *Plasmodium falciparum*, for use in the treatment or prevention of pregnancy-associated malaria.

In certain preferred embodiments, the first family is the parasitic family of *Plasmodium falciparum* whose VAR2CSA protein is characterized by an Id1 interdomain that has as sequence the consensus sequence SEQ ID NO: 11 or that is encoded by the consensus nucleic acid sequence SEQ ID NO: 13, and the second family is the parasitic family of *Plasmodium falciparum* whose VAR2CSA protein is characterized by an Id1 interdomain that has as sequence the consensus sequence SEQ ID NO: 12 or that is encoded by the consensus nucleic acid sequence SEQ ID NO: 14.

In certain embodiments, the second parasitic family of *Plasmodium falciparum* comprises the parasitic line FCR3 and the parasitic line 3D7.

In certain embodiments, a combination according to the invention is characterized in that it consists of three isolated or purified polypeptides, the first isolated or purified polypeptide consisting of the NTS-DBL1x-Id1-DBL2x region or the Id1-DBL2x region of the VAR2CSA protein of the parasitic family of *Plasmodium falciparum* whose VAR2CSA protein is characterized by an Id1 interdomain that has as sequence the consensus sequence SEQ ID NO: 11 or that is encoded by the consensus nucleic acid sequence SEQ ID NO 13, the second isolated or purified polypeptide consisting of the NTS-DBL1x-Id1-DBL2x region or the Id1-DBL2x region of the VAR2CSA protein of the FCR3 line, and the third isolated or purified polypeptide consisting of the NTS-DBL1x-Id1-DBL2x region or the Id1-DBL2x region of the VAR2CSA protein of the 3D7 line.

In certain embodiments, the NTS-DBL1x-Id1-DBL2x region of the VAR2CSA protein of the FCR3 line has the sequence SEQ ID NO: 1 or a homologous sequence of SEQ ID NO: 1, and the NTS-DBL1x-Id1-DBL2x region of the VAR2CSA protein of the 3D7 line has the sequence SEQ ID NO: 5 or a homologous sequence of SEQ ID NO: 5.

In certain embodiments, the Id1-DBL2x region of the VAR2CSA protein of the FCR3 line has the sequence SEQ ID NO: 3 or a homologous sequence of SEQ ID NO: 3, and the Id1-DBL2x region of the VAR2CSA protein of the 3D7 line has the sequence SEQ ID NO: 7 or a homologous sequence of SEQ ID NO: 7.

The present invention also relates to a combination of at least two isolated or purified fusion proteins for use in the treatment or prevention of pregnancy-associated malaria, where the combination corresponds to a combination of at least two isolated or purified polypeptides as described here in which each of the polypeptides is fused to a fusion partner sequence.

In certain embodiments, each of the fusion partner sequences is selected independently from the group consisting of the maltose-binding protein, the signal sequence of the maltose-binding protein, an S-tag, glutathione-S-transferase, thioredoxin, β-galactosidase, streptavidin, dihydrofolate reductase, the signal sequence pelB, the signal sequence ompA, the signal sequence of alkaline phosphatase, green fluorescent protein, toxins, human growth hormone, interleukin-2 (IL-2), granulocyte macrophage colony stimulating factor (GM-CSF), granulocyte colony stimulating factor (G-CSF), calcitonin, interferon beta, interferon alfa, glucagon-like peptide 1 (GLP-1), glucagon-like peptide 2 (GLP-2), toxin PA, parathyroid hormones (PTH (1-34) and PTH(1-84)), butyrylcholinesterase, glucocerebrosidase (GBA), and exendin-4.

The invention also relates to a combination of at least two isolated or purified polynucleotides for use in the treatment or prevention of pregnancy-associated malaria, where each of the isolated or purified polynucleotides encodes a polypeptide as defined above or for a fusion protein as defined above. More precisely, the invention relates to a combination of at least two isolated or purified polynucleotides, the first isolated or purified polynucleotide encoding a first polypeptide consisting of the NTS-DBL1x-Id1-DBL2x region or the Id1-DBL2x region of the VAR2CSA protein of a first parasitic family of *Plasmodium falciparum* or for a first fusion protein comprising the first polypeptide, and containing the elements necessary for expression of said first polypeptide or of said first fusion protein in vitro and/or in vivo; and the second isolated or purified polynucleotide encoding a second polypeptide consisting of the NTS-DBL1x-Id1-DBL2x region or the Id1-DBL2x region of the VAR2CSA protein of a second parasitic family of *Plasmodium falciparum* or for a second fusion protein comprising the second polypeptide, and containing the elements necessary for expression of said second polypeptide or of said second fusion protein in vitro and/or in vivo, for use in the treatment or prevention of pregnancy-associated malaria.

In certain embodiments, the first family is the parasitic family of *Plasmodium falciparum* whose VAR2CSA protein is characterized by an Id1 interdomain that has as sequence the consensus sequence SEQ ID NO: 11 or that is encoded by the consensus sequence SEQ ID NO: 13 and the second family is the parasitic family of *Plasmodium falciparum* whose VAR2CSA protein is characterized by an Id1 interdomain that has as sequence the consensus sequence SEQ ID NO: 12 or that is encoded by the consensus sequence SEQ ID NO: 14.

In certain embodiments, the second parasitic family of *Plasmodium falciparum* comprises the parasitic line FCR3 and the parasitic line 3D7.

In certain embodiments, the combination according to the invention consists of three isolated or purified polynucleotides, the first isolated or purified polynucleotide encoding a first polypeptide consisting of the NTS-DBL1x-Id1-DBL2x region or the Id1-DBL2x region of the VAR2CSA protein of the parasitic family of *Plasmodium falciparum* whose VAR2CSA protein is characterized by an Id1 interdomain that has as sequence the consensus sequence SEQ ID NO: 11 or that is encoded by the consensus sequence SEQ ID NO: 13 or for a first fusion protein comprising the first polypeptide, and containing the elements necessary for expression of said first polypeptide or of said first fusion protein in vitro and/or in vivo; the second isolated or purified polynucleotide encoding a second polypeptide consisting of the NTS-DBL1x-Id1-DBL2x region or the Id1-DBL2x region of the VAR2CSA protein of the FCR3 line or for a second fusion protein comprising the second polypeptide, and containing the elements necessary for expression of said second polypeptide or of said second fusion protein in vitro and/or in vivo; and the third isolated or purified polynucleotide encoding a third polypeptide consisting of the NTS-DBL1x-Id1-DBL2x region or the Id1-DBL2x region of the VAR2CSA protein of the 3D7 line or for a third fusion protein comprising the third polypeptide, and containing the elements necessary for expression of said third polypeptide or of said third fusion protein in vitro and/or in vivo.

In certain embodiments, the NTS-DBL1x-Id1-DBL2x region of the VAR2CSA protein of the FCR3 line has the sequence SEQ ID NO: 1 or a homologous sequence of SEQ ID NO: 1, and the NTS-DBL1x-Id1-DBL2x region of the VAR2CSA protein of the 3D7 line has the sequence SEQ ID NO: 5 or a homologous sequence of SEQ ID NO: 5.

In certain embodiments, the Id1-DBL2x region of the VAR2CSA protein of the FCR3 line has the sequence SEQ ID NO: 3 or a homologous sequence of SEQ ID NO: 3, and the Id1-DBL2x region of the VAR2CSA protein of the 3D7 line has the sequence SEQ ID NO: 7 or a homologous sequence of SEQ ID NO: 7.

In certain embodiments, the second isolated or purified polynucleotide comprises a sequence selected from the group consisting of SEQ ID NO: 2, a homologous sequence of SEQ ID NO: 2, SEQ ID NO: 4, a homologous sequence of SEQ ID NO: 4, SEQ ID NO: 6, a homologous sequence of SEQ ID NO: 6, SEQ ID NO: 8, and a homologous sequence of SEQ ID NO: 8.

In the embodiments where a second and a third isolated or purified polynucleotide are present, the second isolated or purified polynucleotide preferably comprises a sequence selected from the group consisting of SEQ ID NO: 2, a homologous sequence of SEQ ID NO: 2, SEQ ID NO: 4, a homologous sequence of SEQ ID NO: 4, and the third isolated or purified polynucleotide preferably comprises a sequence selected from the group consisting of SEQ ID NO: 6, a homologous sequence of SEQ ID NO: 6, SEQ ID NO: 8, and a homologous sequence of SEQ ID NO: 8.

In another aspect, the invention relates to an immunogenic composition comprising at least one pharmaceutically acceptable vehicle or excipient and at least one combination of polypeptides or of fusion proteins or of polynucleotides according to the invention. Preferably, an immunogenic composition of this kind is characterized in that it is capable of inducing antibodies that completely inhibit the adhesion of erythrocytes infected by *Plasmodium falciparum* to the placental receptor CSA (chondroitin sulfate A).

In a variant of this aspect, the invention also relates to vaccines against pregnancy-associated malaria. In particular, the invention supplies a vaccine comprising at least one combination of polypeptides or of fusion proteins according to the invention, or at least one combination of polynucleotides according to the invention. In certain embodiments, the polynucleotides of the combination present in a vaccine are inserted in at least one plasmid. Preferably, the vaccines according to the invention are characterized in that they are capable of inducing antibodies that completely inhibit the adhesion of erythrocytes infected by *Plasmodium falciparum* to the placental receptor CSA. The vaccines described here may further comprise an adjuvant.

In another variant of this aspect, the invention relates to methods of treating or preventing pregnancy-associated malaria. In particular, the invention supplies a method for inducing a protective immune response against *Plasmodium falciparum* in a human being of the female sex, said method comprising a step of administering an effective amount of an immunogenic composition or of a vaccine described here. The invention also supplies a method of vaccinating a human being of the female sex against *Plasmodium falciparum*, said method comprising a step of administering an effective amount of a vaccine, in particular of a DNA vaccine described here or of a protein vaccine described here. The methods of treating and preventing pregnancy-associated malaria mainly apply to prepubescent girls and to women of reproductive age. In certain preferred embodiments, a method of treating or preventing pregnancy-associated malaria is characterized in that it induces, in human beings of the female sex, antibodies that prevent the adhesion of erythrocytes infected by *Plasmodium falciparum* to the placental receptor CSA. In the methods of treating or preventing pregnancy-associated malaria according to the invention, the immunogenic composition or vaccine may be administered by any suitable route.

In another aspect, the invention relates to a kit for vaccinating against pregnancy-associated malaria comprising at least one combination, or at least one immunogenic composition or at least one vaccine according to the invention and instructions for carrying out vaccination against pregnancy-associated malaria. In certain embodiments, the at least two polypeptides or at least two fusion proteins or at least two polynucleotides of the combination, of the immunogenic composition or of the vaccine are supplied separately in the kit.

A more detailed description of certain preferred embodiments of the invention is given below.

DETAILED DESCRIPTION OF THE INVENTION

In general, the present invention relates to the use of combinations of specific regions of the N-terminal portion of the VAR2CSA protein derived from different parasitic families of *Plasmodium falciparum* in the prevention and/or treatment of pregnancy-associated malaria.

I—NTS-DBL1x-Id1-DBL2x and Id1-DBL2x Polynucleotides and Polypeptides Relating to NTS-DBL1x-Id1-DBL2x and Id1-DBL2x The present invention relates to combinations of at least two polynucleotides or of at least two polypeptides derived from the N-terminal portion of the extracellular domain of VAR2CSA of different parasitic families of *Plasmodium falciparum*, as well as to their applications in the management of pregnancy-associated malaria. In particular, the invention relates to combinations of at least two polynucleotides or of at least two polypeptides derived from the N-terminal region of the extracellular domain of VAR2CSA of two parasitic families of *Plasmodium falciparum* demonstrated by the inventors, and whose segregation takes place in the Id1 interdomain of VAR2CSA.

The first family, which is a recently identified cluster, is characterized by a VAR2CSA protein having an Id1 interdomain having as sequence the consensus sequence SEQ ID NO: 11 or that is encoded by the consensus nucleic acid sequence SEQ ID NO: 13.

```
                                          SEQ ID NO: 11
dY!K.#PYS.EyGKLLkFDNTNAFkESiT.nkNVCsCSgnEKliis#

GSssS.SFGTSfSY#nS!.TSnKRkECkQIKFSGNKNNMNInICSTQ

D.#nLLVkl;LLKgFC#tcdt.iG.VEVVsE#NCEEQYKKLLPcLEK

CT!LnCNECNKTrcKpLKK.#EkWIWgKpkq..aGLQkE
``` where "!" is one of I and V, "#" is one of N, D, Q, E, B, and Z, and "." is either a gap, or a position where no consensus has been attained.

```
                                          SEQ ID NO: 13
gaTTAtaTAAAGgaTgATCCTTATTCC.cAGAAtATGGAAAACTATT

AAaaTTTGATAACACTAATGCATTTAaaGAAtcTatAACAT.TaAcA

AaAATGTATGTTcTTGtAGtggtaaTGAAAAATtGatcAtAtCaGAa

GGATCATcAaGTTCA.GTTCTTTTGGAACATCgTtTTCTTATgAAAa

TAGTgTAA...CATCaAAtAAgAGAAAaGAATGTaaACAAATAAAAT

TTAGTGGTAATAAAAATAATATGAATATTAAtATATGTT.CCACGCA

GGAT..aAcAAtTTgTTGGTAaAATTagAGGAgTTATTGAAAgGTTT

TTGCgATAcATgTGacacTgaTAtTGGAG...TTGAGGTAGTTaGTG

AGaAtAATTGCGAAGAGCAATATAAAAAACTGCTCCCCTgTCTTGAG

AAATGcACTgTTTTGAaTTGTAATGAATGCAATAAAACTcgATgTAA

AccaTTAAAAAAGgaacAAGAAAaATGGATtTGGggtAAAccaaaac aagaagctGcaGGgTTgCAAaAAGAa
``` where "." is either a gap, or a position where no consensus has been attained.

The second family, which is a cluster comprising the FCR3 line and the 3F7 line, is characterized by a VAR2CSA protein having an Id1 interdomain having as sequence the consensus sequence SEQ ID NO: 12 or that is encoded by the consensus nucleic acid sequence SEQ ID NO: 14.

```
                                          SEQ ID NO: 12
.Y!KdDPYsaEY.TKLSFIlNsSDa#tsSeki.knnDEvCNcNESeI ssVgqaqtS.psS#KtCiTHSsIkaNKKKyCKdVKLG!r#nDKdLk!

CVIEdtsLsGV#NCCoqDlLgiLQEncsD.NksgSSSNGSC#nkn;.

C#knL#kvlASLtNgYKc#KCKSeqSkknn..WiWkK.sGne.GLQk

E
``` where "!" is one of I and V, "#" is one of N, D, Q, E, B, and Z, and "." is either a gap, or a position where no consensus has been attained.

```
                                          SEQ ID NO: 13
aaTTAtaTAAAgGaTGATCCTTATTcCgcAGAATATgcAACtAAATT

ATCATTTATTttAAATtCATCAGATgCtaAtAcTtCGTCTGaAaaAa ta.aAAAaaATaATGATGAAGtATGTAACtgTAATGAATCAGaAATT tCATctGTTGgACaGGcAcaAAcATCgGgTccgTcGTCgaAtAAAaC ATGTAtCACACATAGcTccATAaaAgCTAATAAGAAAAAAGtATGTA AAgATGTAAAGTTGGGTgTTcgTgAaAAtGATAAaGaTTTGAaAaTA TGCGTAATTGAGgAcactTCCTTaaGTGGTGTTGAaAATTGTTGTTg CcAAGATTTaTTGgGAATtCTTCAAGAAaaTtGtAgTGATAAtAA.c .a.GTGgATCTAGTTCTAATGGTAGTTGTgATAAcAAaAaTcAGGAa G.ATGTgAAAaaAAtTTAGAaaAAGtacTTGCATCTTTAactAATgG TTATAAAtgCgAcAAATGTAAATCTGgAacATCAA.Aa....TAAcA AaAaaTGGAtATGGAaAAAAT.CtcTGGTaatgaagaaGGATTACAA aAaGAA
``` where "." is either a gap, or a position where no consensus has been attained.

The second parasitic family of *Plasmodium falciparum* demonstrated by the inventors comprises the parasitic line FCR3 and the parasitic line 3D7. The gene encoding VAR2CSA was isolated in several parasitic strains including FCR3 (GenBank Accession Number: AY372123) and 3D7 (GenBank Accession Number: AE014188.3) and sequenced. The corresponding VAR2CSA protein was deduced (GenBank Accession Number: AAQ73926.1 for the FCR3 line and GenBank Accession Number: AAN36095.1 for the 3D7 line).

The term "isolated or purified", as used here for qualifying a polypeptide or polynucleotide, denotes a polypeptide or polynucleotide which, owing to its origin or its manipulation, is separated from at least certain components with which it is naturally associated. Alternatively or additionally, "isolated or purified" means a polypeptide or polynucleotide that is produced or synthesized by humans.

The terms "NTS-DBL1x-DBL2x" and "NTS-DBL1x-Id1-DBL2x" are used here indiscriminately. They denote the region of VAR2CSA consisting of the domains: Duffy-binding-like domain 1x (DBL1x), interdomain 1 (Id1) and Duffy-binding-like domain 2x (DBL2x). The term "Id1-DBL2x" denotes the region of VAR2CSA consisting of the interdomain 1 (Id1) and the Duffy-binding-like domain 2x (DBL2x).

In certain preferred embodiments, the polypeptide of a combination according to the invention consisting of the NTS-DBL1x-Id1-DBL2x region of the VAR2CSA protein of the parasitic FCR3 line has the sequence SEQ ID NO: 1, a homologous sequence of the sequence SEQ ID NO: 1 or a modified sequence of the sequence SEQ ID NO: 1; and the polypeptide of a combination according to the invention consisting of the NTS-DBL1x-Id1-DBL2x region of the VAR2CSA protein of the parasitic line 3D7 has the sequence SEQ ID NO: 5, a homologous sequence of the sequence SEQ ID NO: 5 or a modified sequence of the sequence SEQ ID NO: 5.

In other preferred embodiments, the polypeptide of a combination according to the invention consisting of the Id1-DBL2x region of the VAR2CSA protein of the parasitic FCR3 line has the sequence SEQ ID NO: 3, a homologous sequence of the sequence SEQ ID NO: 3 or a modified sequence of the sequence SEQ ID NO: 3, and the polypeptide of a combination according to the invention consisting of the Id1-DBL2x region of the VAR2CSA protein of the parasitic line 3D7 has the sequence SEQ ID NO: 7, a homologous sequence of the sequence SEQ ID NO: 7 or a modified sequence of the sequence SEQ ID NO: 7.

The terms "peptide", "protein", "peptide sequence", "polypeptide sequence", and "polypeptide" are used here indiscriminately. These terms are intended to denote a precise chain of amino acids, modified or not, bound to one another by peptide bonds.

"Homologous peptide sequence of the sequence SEQ ID NO: X" means any peptide sequence that differs from the sequence SEQ ID NO: X by substitution, deletion, and/or insertion of an amino acid or of a reduced number of amino acids, at positions such that these homologous peptide sequences have substantially the same biological properties as the NTS-DBL1x-Id1-DBL2x region or the Id1-DBL2x region of VAR2CSA of the FCR3 line or 3D7 line. Preferably, a homologous peptide sequence of this kind has a percentage identity such that it is identical to at least 75% of the sequence SEQ ID NO: X, preferably at least 85%, even more preferably at least 95%.

"Percentage identity" or "homology" between two nucleotide sequences or two peptide sequences denotes a percentage of nucleotides or of amino acid residues that are identical between the two sequences to be compared, obtained after optimal alignment. This percentage is purely statistical and the differences between the two sequences are distributed at random and over the entire length of the sequence. The terms "optimal alignment" and "best alignment", which are used interchangeably here, denote the alignment for which the percentage identity determined as described below is highest. Optimal alignment of the sequences, necessary for comparison, may be carried out manually or by means of computer software (GAP, BEST-FIT, BLASTP, BLASTN, FASTA, and TFASTA, which are available either on the NCBI website, or in the Wisconsin Genetics Software Package, Genetics Computer Group, Madison, Wis.). The percentage identity between two nucleotide sequences or two peptide sequences is calculated by determining the number of identical positions for which the nucleotide or the amino acid residue is identical between the two sequences, by dividing this number of identical positions by the total number of positions compared and by multiplying the result obtained by 100.

"Modified peptide sequence of the sequence SEQ ID NO: X" means any polypeptide sequence that differs from SEQ ID NO: X by one or more modifications, for example post-translational cellular modifications (e.g. "editing", glycosylation, sulfation, etc.).

The present invention also relates to combinations of at least two fusion proteins for treating or preventing pregnancy-associated malaria, where each of the fusion proteins consists of an isolated or purified polypeptide as defined above fused to a given fusion sequence partner.

Here, "fusion sequence partner" means a peptide sequence that endows the fusion protein with one or more desirable properties. Thus, a fusion sequence partner may consist of a protein that promotes expression of the NTS-DBL1x-Id1-DBL2x region or of the Id1-DBL2x region in the host cell during preparation of the fusion protein, and/or of a protein that facilitates purification of the fusion protein, and/or of a protein that increases the stability (e.g. plasma stability) of the fusion protein (by comparison with a sequence corresponding to unfused NTS-DBL1x-Id1-DBL2x or Id1-DBL2x), and/or of a protein that promotes administration of the fusion protein to the subject being vaccinated, and/or of a protein that increases the required therapeutic effect (for example by increasing the immune and vaccine response) and/or of a protein displaying biological or therapeutic activity.

The fusion partners that may be used in the context of the present invention include, without limitation, maltose-binding protein, the signal sequence of maltose-binding protein, polyhistidine segments capable of binding metal ions, an S-Tag, glutathione-S-transferase, thioredoxin, β-galactosidase, streptavidin, dihydrofolate reductase, the signal sequence pelB, the signal sequence ompA, the signal sequence of alkaline phosphatase, green fluorescent protein, a toxin such as, for example, the enterotoxin LT of *E. coli* or its subunit B, a domain of the C fragment of tetanus toxin, the cholera toxin or its subunit B, CTA1-DD. Other fusion partners may be human growth hormone, an immunostimulating cytokine such as: interleukin-2 (IL-2), a growth factor such as granulocyte macrophage colony stimulating factor (GM-CSF), granulocyte colony stimulating factor (G-CSF), peptides or hormones such as calcitonin, interferon beta, interferon alfa, glucagon-like peptide 1 (GLP-1), glucagon-like peptide 2 (GLP-2), PA toxin, parathyroid hormone (PTH(1-34) and PTH(1-84)), butyrylcholinesterase, glucocerebrosidase (GBA), and exendin-4.

The novel cluster demonstrated by the present inventors is characterized by a VAR2CSA protein whose Id1 interdomain has as sequence the consensus sequence SEQ ID NO: 11 or is encoded by the consensus sequence SEQ ID NO: 13. The other cluster demonstrated by the present inventors is characterized by a VAR2CSA protein whose Id1 interdomain has as sequence the consensus sequence SEQ ID NO: 12 or is encoded by the consensus nucleic acid sequence SEQ ID NO: 14. "Consensus sequence" means an idealized sequence of a given region of a protein in which each position represents the amino acid encountered most frequently. The consensus sequences were established by comparing real sequences.

The present invention also relates to combinations of at least two isolated or purified polynucleotides for use in the treatment or prevention of pregnancy-associated malaria, where each of the isolated or purified polynucleotides encodes a polypeptide as defined above or for a fusion protein as defined above, and contains the elements necessary for expression, in vitro and/or in vivo, of said polypeptide or of said fusion protein. More precisely, the invention relates to a combination of at least two polynucleotides, where each of the polynucleotides encodes a polypeptide consisting of the NTS-DBL1x-Id1-DBL2x region or the Id1-DBL2x region of the VAR2CSA protein of a given parasitic line or family of Plasmodium falciparum or for a fusion protein comprising said polypeptide, and where each of the isolated or purified polynucleotides contains the elements necessary for expression of said polypeptide or of said fusion protein in vitro or in vivo.

The terms "nucleotide sequence", "nucleic acid", "nucleic acid sequence", "polynucleotide" and "oligonucleotide" are used here indiscriminately. These terms denote a precise chain of nucleotides, modified or not, allowing a region of a nucleic acid to be defined, and which may correspond both to a double-stranded DNA or a single-stranded DNA and to transcription products of these DNAs.

The elements necessary for expression of a nucleotide sequence in vivo include, for example, a promoter, a transcription start region, and a transcription termination region, which are functional in a mammalian cell, preferably a human cell. Moreover, sequences that increase gene expression, such as introns, "enhancer" sequences and "leader" sequences, are often necessary for expression of a sequence encoding an immunogenic protein. As is known in the prior art, these elements are preferably bound operationally to the nucleotide sequence that must be expressed. The terms "linked operationally" and "linked in an operational manner" are used indiscriminately and refer to a functional link between the regulatory sequences and the nucleic acid sequence that they control.

Examples of promoters useful in the context of the present invention include non-exhaustively the promoters of the SV40 virus, of the mouse mammary tumor virus (MMTV), of the HIV virus, of the Moloney virus, of the cytomegalovirus (CMV), of the Epstein-Barr virus (EBV), of the Rous sarcoma virus (RSV), as well as the promoters of human genes such as the human gene of actin, of myosin, of hemoglobin, of muscular creatine and of metallothionein.

The construction of a polynucleotide consisting of a given nucleotide sequence and of the elements necessary for expression of this nucleotide sequence is within the competence of a person skilled in the art.

In certain preferred embodiments, the nucleotide sequence of the polynucleotide that encodes the NTS-DBL1x-Id1-DBL2x region of the VAR2CSA protein of the FCR3 line has the sequence SEQ ID NO: 2 or a homologous sequence of SEQ ID NO: 2, and the nucleotide sequence of the polynucleotide that encodes the NTS-DBL1x-Id1-DBL2x region of the VAR2CSA protein of the 3D7 line has the sequence SEQ ID NO: 6 or a homologous sequence of SEQ ID NO: 6.

In other preferred embodiments, the nucleotide sequence of the polynucleotide that encodes the Id1-DBL2x region of the VAR2CSA protein of the FCR3 line has the sequence SEQ ID NO: 4 or a homologous sequence of SEQ ID NO: 4, and the nucleotide sequence of the isolated or purified polynucleotide that encodes the Id1-DBL2x region of the VAR2CSA protein of the 3D7 line has the sequence SEQ ID NO: 8 or a homologous sequence of SEQ ID NO: 8.

"Homologous nucleotide sequence of the sequence SEQ ID NO: X" means any nucleotide sequence that differs from the sequence SEQ ID NO: X by substitution, deletion, and/or insertion of a nucleotide, or of a reduced number of nucleotides, at positions such that these sequences encode the same polynucleotide or substantially the same polynucleotide as SEQ ID NO: X. A "homologous nucleotide sequence of the sequence SEQ ID NO: X" is preferably a homologous sequence of SEQ ID NO: X that results from degeneration of the genetic code.

Preparations of Polynucleotides and Polypeptides Relating to NTS-DBL1x-Id1-DBL2x and Id1-DBL2x The polynucleotides, fusion proteins and polypeptides of the present invention may be prepared by any suitable method.

The techniques for isolating or cloning a gene or a nucleotide sequence encoding a specific domain of a protein are known in the prior art and include isolation from genomic DNA, preparation from complementary DNA, or a combination of these methods. The cloning of a gene, or of a nucleotide sequence encoding a specific domain of a protein, starting from a genomic DNA may be carried out for example using a polymerase chain reaction (PCR) or by screening expression libraries to detect cloned DNA fragments with identical structural characteristics (Innis et al., "PCR: A Guide to Method and Application", 1990, Academic Press: New York). Other methods of amplification of nucleic acids known by a person skilled in the art may be used, for example a ligase chain reaction (LCR), a ligation activated transcription (LAT) and the NASBA (nucleic acid sequence based amplification) technique. It is also possible to use a method of chemical synthesis to prepare a nucleotide sequence. The methods of complete chemical synthesis of strands of DNA or of RNA are known by a person skilled in the art, and use commercial automated synthesizers.

The methods for preparing a peptide sequence include chemical methods (R. B. Merrifield, J. Am. Chem. Soc. 1963, 85: 2149-2154; "Solid Phase Peptide Synthesis", Methods in Enzymology, G. B. Fields (Ed.), 1997, Academic Press: San Diego, Calif.), and recombinant methods (Sambrook et al., Molecular Cloning: A Laboratory Manual, $2^{nd}$ Ed., 1989, Cold Spring Harbor Press: Cold Spring, N.Y.) using host cells (especially in the case of fusion proteins).

Composition of a Combination

In a combination according to the invention, the polynucleotides or fusion proteins or polypeptides may be present in any proportions. In the embodiments where a combination of the invention only consists of two components (two polypeptides, two fusion proteins or two polynucleotides), the two components may in particular be present in equal amounts. In the embodiments where a combination of the invention consists of three components (three polypeptides, three fusion proteins or three polynucleotides), the three components may in particular be present in equal amounts.

The respective amounts of the components of a combination may be determined and/or optimized by a person skilled in the art as a function of the use of the combination and/or of the nature of its components.

II—Immunogenic Compositions and Vaccines

The combinations according to the invention are particularly suitable for use as medicinal products in the management of pregnancy-associated malaria. In fact, as the inventors have demonstrated, these combinations make it possible to induce anti-adherence antibodies with a broad spectrum of activity. Accordingly, they may be used, as they are or in a modified form, as an immunogenic composition or vaccine.

A suitable modification of the polypeptides contained in a combination according to the invention is the production of conjugates. The latter comprise at least one of the polypeptides of a combination according to the invention, bound to a support. The conjugates may be obtained by coupling via a covalent bond between a polypeptide and a physiologically acceptable nontoxic, natural or synthetic support that is able, for example, to increase the immunogenic character of the polypeptide.

Regarding the conjugates, we may mention as an example application WO 2006/124712, which describes methods for preparing conjugates comprising a plurality of antigenic peptides of *Plasmodium falciparum* bound to a supporting protein improving the immunogenicity of said antigens.

The preferred supports according to the invention are selected from the viral particles, lipids, for example lipids of the C16-C18 type, polylysines, poly(DL-alanine)-poly(lysine)s, nitrocellulose, polystyrene microparticles, microparticles of latex beads, biodegradable polymers, microparticles of polyphosphoglycans, supporting proteins such as OMPC (outer membrane protein complex of *Neisseria meningitidis*) or improved OMPC, BSA (bovine serum albumin), TT (tetanus toxoid), ovalbumin, KLH (keyhole limpet hemocyanin), THY (bovine thyroglobulin), HbSAg and HBcAg of hepatitis B virus, rotavirus capsid proteins, protein L1 of human papilloma virus, VLP (virus like particle) of type 6, 11 and 16, tuberculin PPD (purified protein derivative).

Immunogenic Compositions

An immunogenic composition according to the invention comprises, in addition to a combination described here, a pharmaceutically acceptable vehicle or excipient. The term "pharmaceutically acceptable vehicle or excipient" denotes any vehicle or medium that does not interfere with the effectiveness of the biological activity of the active principle of the composition, and that is not toxic for an individual at the concentration at which it is administered. The use of such vehicles or excipients for formulating active substances is well known in the art ("*Remington's Pharmaceutical Sciences*", E. W. Martin, 18$^{th}$ Ed., 1990, Mack Publishing Co.: Easton, Pa.).

The formulation of an immunogenic composition of the present invention may vary as a function of the route of administration and the dosage. After formulation with at least one pharmaceutically acceptable vehicle or excipient, an immunogenic composition of the invention may be administered in any form suitable for administration to a human being, for example in solid or liquid form. A person skilled in the art knows how to select the most suitable vehicles and excipients for preparing a certain type of formulation. Thus, for example, excipients such as water, 2-3-butanediol, isotonic solution of sodium chloride, synthetic mono- or diglycerides, and oleic acid are often used for formulating injectable preparations. Liquid compositions, including emulsions, microemulsions, solutions, suspensions, syrups, etc., may be formulated in the presence of solvents, solubilizers, emulsifiers, oils, fatty acids and other additives such as suspending agents, preservatives, viscosity modifiers, etc. The solid compositions for administration by the oral route may be formulated in the presence of an inert excipient such as sodium citrate, and optionally additives such as binders, humectants, disintegrants, absorption accelerators, lubricants, etc.

According to a preferred embodiment, the immunogenic compositions and the vaccines of the invention may comprise one or more adjuvants used in combination. Conventional adjuvants such as Montanide and/or alum may be used. However, other adjuvants such as QS21, SBQS2, MF59, mLT, PHL, CpG DNA, calcium phosphate, dehydrated calcium sulfate, PLG, CT, LTB, CT/LT, AS02A are also suitable.

The immunogenic compositions and vaccines according to the invention may further comprise at least one specific antigen of the preerythrocyte stages (CSP, TRAP, LSA-1, LSA-3, SALSA, STARP, EXP-1), asexual erythrocyte stages (MSP-1, MSP-3, AMA-1, EBA-175, GLURP, MSP-2, MSP-4, MSP-5, RAP-2, RESA, PfEMP-1, synthetic GPI toxin) or sexual stages (PfS25).

Vaccines, Polypeptide Vaccines, DNA Vaccines

In general, a vaccine against pregnancy-associated malaria according to the invention comprises at least one combination described here and is used for inducing, in the vaccinated subjects, antibodies that inhibit cytoadherence to CSA. In particular, the invention relates to a DNA vaccine (also called plasmid vaccine or polynucleotide vaccine) against pregnancy-associated malaria. The invention also relates to a protein vaccine (also called polypeptide vaccine) against pregnancy-associated malaria.

Protein Vaccines

The present invention therefore relates to a protein vaccine comprising a combination of at least two polypeptides as described above or a combination of at least two fusion proteins as described above.

Preparation of a protein vaccine, which may be done by a chemical or biochemical route (recombinant protein), is within the competence of a person skilled in the art.

A protein vaccine may be administered by any suitable route, for example by the intravenous, subcutaneous, intradermal, oral, topical or systemic route.

DNA Vaccines

The present invention also relates to a DNA vaccine against pregnancy-associated malaria. The purpose of genetic vaccination or DNA vaccination is to induce an immune response and consists of introducing a gene or a polynucleotide sequence encoding a vaccinal antigen or a purified DNA plasmid containing a sequence encoding the vaccinal antigen directly into certain cells of the body. The cells in question are, in the example of the invention, muscle cells, but any other type of cell may be suitable, for example cells of the skin. Administration is performed, non-exclusively, by intramuscular injection or by "bombardment" of particles on the skin or else by the nasal route. The DNA penetrates into the muscle cells, cells of the skin or others; and these cells then synthesize the antigen themselves. The antigen is presented to the immune system and triggers a response (production of antibodies which, during infection, are capable of specifically recognizing this antigen on the parasite). The vaccine is therefore produced locally by the body of the individual to be immunized. This method of vaccination, which is simple and inexpensive, offers important advantages in terms of efficacy: the antigen thus produced is generally in the form of its native peptide sequence, fused or not to one or more peptide sequences (fusion partners). In particular, it is produced over an extended period by the body's cells, and this long-lasting presentation of the antigen to the immune system should make it possible to avoid the need for booster doses. Moreover, DNA vaccines are chemically defined and thermally stable, which reduces the need to maintain the cold chain.

The present invention therefore relates to a DNA vaccine comprising a combination of at least two polynucleotides as described above. A polynucleotide of a combination of the invention may be bare DNA, in particular a circular vaccine plasmid, supercoiled or not, or a linear DNA molecule, incorporating and expressing in vivo a nucleotide sequence encoding the NTS-DBL1x-Id1-DBL2x region or for the Id1-DBL2x region of the VAR2CSA protein of the FCR3 line or 3D7 line or of the new cluster. "Bare DNA" means, as is commonly accepted at present, a DNA transcription unit in the form of a polynucleotide sequence comprising at least one nucleotide sequence encoding a vaccinal antigen and the elements necessary for expression thereof in vivo. The polynucleotides of a combination according to the invention may advantageously be inserted in a plasmid of type DNA-CSP, Nyvac pf7, VR1020, VR1012, etc.

It is also envisaged that the bare DNA is incorporated in a medicinal product vector. Examples of suitable medicinal product vectors include, non-exhaustively, biodegradable microcapsules, immunostimulating complexes, liposomes, cationic lipids and genetically attenuated live vectors such as viruses and bacteria.

A DNA vaccine of the invention may also be administered in conjunction with an agent that improves the penetration of the genetic material of the vaccine into the cells that are treated. Thus, the DNA vaccine may be formulated to contain such an agent or may be administered at the same time as such an agent. Examples of agents that improve the penetration of the genetic material of the vaccine into the treated cells include, non-exhaustively, benzoic acid esters, anilides, amidines, urethanes, and hydrochloride salts thereof (U.S. Pat. No. 6,248,565). Administration of the DNA to the cells may be promoted by chemical vectors (for example, cationic polymers or cationic lipids), physical techniques such as electroporation, sonoporation, magnetofection, etc., or viral vectors such as the adenovirus-associated viruses, etc.

III—Uses of the Immunogenic Compositions and Vaccines

The immunogenic compositions and the vaccines may be used advantageously for immunizing human beings of the female sex (prepubescent girls and women of reproductive age) in the context of prophylactic therapy of pregnancy-associated malaria.

Consequently, the invention also relates to methods of treating or preventing pregnancy-associated malaria. In particular, the invention supplies a method for inducing a protective immune response against *Plasmodium falciparum* in a human being of the female sex, said method comprising a step of administering an effective amount of an immunogenic composition or of a vaccine described here. The invention also supplies a method of vaccinating a human being of the female sex against *Plasmodium falciparum*, said method comprising a step of administering an effective amount of a vaccine, in particular a DNA vaccine or a protein vaccine described here.

In certain preferred embodiments, a method of treating or preventing pregnancy-associated malaria is characterized in that it induces, in human beings of the female sex, antibodies that prevent the adhesion of erythrocytes infected by *Plasmodium falciparum* to the placental receptor CSA.

In the methods of treating or preventing pregnancy-associated malaria according to the invention, the immunogenic composition or vaccine may be administered by any suitable method (oral, parenteral, mucosal route). In certain embodiments, a DNA vaccine is administered by the intramuscular, intradermal, or mucosal route. In other embodiments, a protein vaccine is administered for example by the intravenous, subcutaneous, intradermal, oral, topical or systemic route.

An immunogenic composition or a vaccine according to the invention may be administered in a single dose or in several doses. A person skilled in the art will be able to determine the effective dose of immunizing protein or of DNA to be used in each immunization or vaccination protocol.

IV—Kits

The present invention also relates to a kit for prophylaxis against pregnancy-associated malaria. More specifically, the kit comprises materials useful for carrying out vaccination by the method of the invention. In general, a kit comprises a combination, an immunogenic composition or a vaccine according to the invention, and instructions for carrying out vaccination against pregnancy-associated malaria. Optionally, the kit may further comprise means for performing vaccination.

In certain embodiments, a kit according to the invention is configured in such a way that the components of a combination according to the invention are supplied separately (for example in different containers). Such a configuration allows both simultaneous administration and sequential administration of the components of the combination. Here, "simultaneous administration" means administration of the components, together or separately, at approximately the same time (for example, at an interval of 5, 10, 15 or 30 minutes from one other). Here, "sequential administration" means administration of the components separately and at different times (for example at different times on the same day, or with an interval of one or more days).

The kit may comprise reagents or solutions for preparing the composition to be administered. The various components of the kit may be supplied in solid form (for example in lyophilized form) or in liquid form. A kit may optionally include a container containing each of the reagents or solutions, and/or containers (test tubes, bottles, etc.) for carrying out preparation of the composition to be administered. Finally, a notice in the form prescribed by a government agency regulating the sale and use of pharmaceutical products may be included in the kit.

Unless they are defined otherwise, all the technical and scientific terms used here have the same meaning as that commonly understood by an ordinary specialist in the field to which this invention belongs. Moreover, all the publications, patent applications, all the patents and all other references mentioned here are incorporated by reference.

The following examples and the figures are presented for illustrating certain embodiments of the procedures described above and must in no case be regarded as a limit to the scope of the invention.

EXAMPLES

The following examples describe certain embodiments of the present invention. However, it is understood that the examples are only presented for purposes of illustration and they do not limit in any instance the scope of the invention.

It has been demonstrated that antibodies to constructs corresponding to a region of the N-terminal portion of VAR2CSA of a single parasitic variant can only inhibit 70% of the adherence of isolates from pregnant women to CSA (Bigey et al., J Infect Dis., 2011, 204: 1125-1133; Bordbar et al., Vaccine, 2012, 30: 1343-1348). The inventors had previously identified a dimorphic region in the DBL2x domain of VAR2CSA (Sander et al., PLoS One, 2009, 4: e6667), leading to two distinct phylogenetic categories of type FCR3 and of type 3D7. In the study presented below, the inventors studied the prevalence of the types of dimorphic variant of DBL2x among the *Plasmodium falciparum* parasites isolated from samples obtained from pregnant women in Benin and the capacity for inhibiting the adhesion of specific antibodies induced against the NTS-DBL1x-Id1-DBL2x region of each serotype on the infected erythrocytes isolated from pregnant women.

Methods and Materials Used

*Plasmodium falciparum* Isolates.

Pregnant women were only included in the present study after their written consent had been obtained. The study was approved by the Consultative Committee of Deontology and Ethics of the IRD (Institut de Recherche pour le Développement: Research Institute for Development), and the ethics committee of the health sciences faculty (University of Abomey-Calavi, Benin). All the procedures used in the present study comply with European and National regulations. The procedure for animal immunization complies with the directive of FELASA (Federation of Laboratory Animal Science Associations) and was approved by the Ethics Committee with respect to animal experiments affiliated to the Descartes University, Paris.

*Plasmodium falciparum* Isolates.

The field samples of infected erythrocytes were obtained from pregnant women at the Suru Léré maternity hospital in the Eastern region of Cotonou. The study site is characterized by hyperendemic malaria in the lagoon region and a high rate of malaria transmission with two peaks corresponding to the two rainy seasons (Akogbeto et al., Parasitologia, 1992, 34: 147-154). Peripheral venous blood was collected in Vacutainers containing the anticoagulant citrate-phosphate-dextrose-adenine (CPDA), during prenatal visits and at the moment of childbirth. The erythrocytes were separated from the plasma and washed with RPMI 1640 (Lonza). 200 μL of red blood cell residues were homogenized in 10 volumes of TRIzol reagent (Invitrogen) and frozen at −80° C. until the moment of extraction of the total RNA or frozen at −20° C. until the moment of extraction of the total DNA. The residues of the erythrocytes infected by parasites at the ring (or young trophozoite) stage were immediately cultured in vitro to obtain aged trophozoites as described previously (Trager et al., Science, 1976, 193: 673-675). Briefly, the isolates were cultured in containers containing RPMI 1640 with addition of HEPES and L-glutamine (Lonza Biowhittaker), 0.3 g/L 1-glutamine, 0.05 g/L gentamicin, 5 g/L Albumax. The culture vessels were placed under an atmosphere of a mixture of 92.5% $N_2$, 2% $O_2$ and 5.5% $CO_2$ and were incubated at 37° C. for not more than 48 hours before the assays. The parasitic laboratory strains FCR3, HB3 and NF54 were cultured in O+ erythrocytes and were selected after several panning steps for the BeWo cell line as described previously (Haase et al., Infect. Immune., 2006, 74: 3035-3038).

Extraction of DNA and Msp Genotyping.

The DNA was extracted from 100 μL of blood sediment with the GeneJet Genomic Purification kit (Fermentas) according to the manufacturer's recommendations. The genes msp1 and msp2 were amplified by nested PCR using specific primers (Snounou et al., Trans R Soc Trop Med Hyg, 1999, 93: 369-374). The multiplicity of infection (MOI) was determined for each sample.

Extraction of RNA, Synthesis of cDNA and Genotyping of the DBL2x.

The RNAs were extracted from frozen samples preserved in TRIzol reagent (Invitrogen) according to the manufacturer's recommendations. The total RNAs were treated with DNAse I (Invitrogen) for 15 minutes at room temperature according to the manufacturer's recommendations to remove any potential contamination by genomic DNA (gDNA). Absence of gDNA in the samples of RNA was confirmed by absence of amplification after 40 cycles of real-time PCR with primers targeting the housekeeping gene seryl-tRNA synthetase (Salanti et al., Mol Microbiol, 2003, 49: 179-191). Reverse transcription of the RNA (without DNA) was performed with Thermoscript (Invitrogen) and random hexameric primers for 1 hour at 50° C. in a total volume of 20 μL according to the manufacturer's recommendations.

For genotyping of the dimorphic sequence motif (DSM) in the DBL2x domain of VAR2CSA of the *Plasmodium falciparum* isolates (Sander et al., PLoS One, 2009, 4: e6667), this domain was selected for amplifying the cDNA of each isolate with a primer pair (5'-TTAYC-CCCAAGAACACA-3' and 5'-TTTTAAATTTTTTCCAT-GAA-3'). The reactions were carried out with high-fidelity Fusion Taq Polymerase (to obtain higher yields and lower mutation rates) in the following conditions: 94° C. for 1 minute, followed by 35 cycles at 94° C. for 30 seconds, 50° C. for 30 seconds and 68° C. for 50 seconds, and a final extension at 68° C. for 10 minutes. The PCR products were digested with the restriction enzymes BstCI (which cut the DSMs of type FCR3) and Hppy188I (which cut the DSMs of type 3D7) for 1 hour at 50° C. and 37° C., respectively. The digested products were separated by electrophoresis on 1.5% agarose gel.

Production of the Antibodies and Preparation of the IgGs.

The fragment NTS-DBL1x-Id1-DBL2x and the entire sequence of the optimized var2csa gene of the parasite lines FCR3 and 3D7 were used for producing specific antiVAR2CSA IgGs, by DNA vaccination as described previously (Bigey et al., J Infect Dis., 2011, 204: 1125-1133). Briefly, the DNA sequences were cloned into a vector derived from pVax1 and fused to the signal sequence mEPO as described previously (Trollet et al., Infect Immune., 2009, 77: 2221-2229). Immunizations were performed on female Swiss mice aged 6 weeks and on New Zealand rabbits (Janvier-France). The mice were anesthetized by intraperitoneal injection with a ketamine-xylazine mixture and in the case of the rabbits, injection was carried out at 5 sites along each longissimus dorsi muscle. DNA transfer was performed by transcutaneous electric pulses applied by two stainless steel electrodes placed at each injection site. The animals were immunized on days 0, 30 and 60, and the antisera were collected on days 0 and 15 after each immunization. The total IgGs were purified in the final mouse or rabbit serum sample on a Hi-Trap column on which the corresponding recombinant protein had been coupled according to the manufacturer's recommendations (GE Healthcare).

Flow Cytometry.

The reactivity of the IgGs purified toward the surface of the erythrocytes infected by *Plasmodium falciparum* was analyzed by flow cytometry (FACS Calibur) as described previously (Magistrado et al., Vaccine, 2011, 29: 437-443). Briefly, the infected erythrocytes adhering to CSA (FCR3-Bewo and HB3-Bewo) and the parasitic field isolates were enriched by exposure to a high-intensity magnetic field (VarioMACS and CS columns, Miltenyi). For each assay, $2 \times 10^5$ infected erythrocytes were labeled with ethidium bromide, and exposed sequentially to a rabbit IgG, and then to an anti-rabbit antibody conjugated to FITC (Invitrogen). The data were acquired and analyzed, and the median fluorescence intensity (MFI) was determined. The labeling of the surface of VAR2CSA is regarded as positive if the MFI ratio is greater than 1.2 (MFI with IgG post-immunization on day 75/MFI with IgG pre-immunization on day 0) as described by Magistrado et al. (Vaccine, 2011, 29: 437-443).

Adhesion Inhibition Assays.

The capacity of the antibodies for inhibiting adhesion of the infected erythrocytes to chondroitin sulfate (CSPG) was determined by an assay in Petri dishes described previously (Bigey et al., J Infect Dis., 2011, 204: 1125-1133). Briefly, Petri dishes (Falcon 351029) were covered with 100×15 mm spots of 20 μL of 5 mg/mL CSPG-Decorin (Sigma) or of 10 μg/mL of bovine serum albumin (BSA) diluted in PBS. The spots were incubated overnight at 4° C. in a humid chamber. Each spot was blocked with 3% BSA in PBS for 30 minutes at 37° C. Suspensions enriched with erythrocytes infected with aged trophozoites were obtained by filtration on a magnetic column (VarioMACS, Miltenyi). The suspension, the parasite density of which was adjusted to 20% in $1 \times 10^5$ cells, was then blocked for 30 minutes at room temperature (RT) in 3% BSA solution diluted in RPMI. The erythrocyte preparation was incubated with purified IgGs (0.25 mg/mL) or 500 μg/mL of soluble CSA (Sigma), and the cells were then left to adhere for 15 minutes at room temperature on Petri dishes precoated with different ligands. The nonadhering cells were removed by an automatic washing system. The spots were fixed with 1.5% of glutaraldehyde in PBS, stained with Giemsa solution and the adhering infected erythrocytes were counted using a microscope.

LEGENDS OF THE FIGURES

FIG. 1 is a graph showing the distribution of the dimorphic sequence signatures of the DBL2x region of VAR2CSA among the parasites infecting pregnant women. The dimorphic sequence motif (DSM) in DBL2x which distinguishes the alleles of VAR2CSA in two subgroups (types 3D7 and FCR3) were genotyped in parasites collected from pregnant women in Benin. The proportions of type 3D7 (white histograms), type FCR3 (shaded histograms) and of mixture of the two genotypes (black histograms) are shown. The multiplicity of infection (MOI) is stated for each category.

Figure 2:
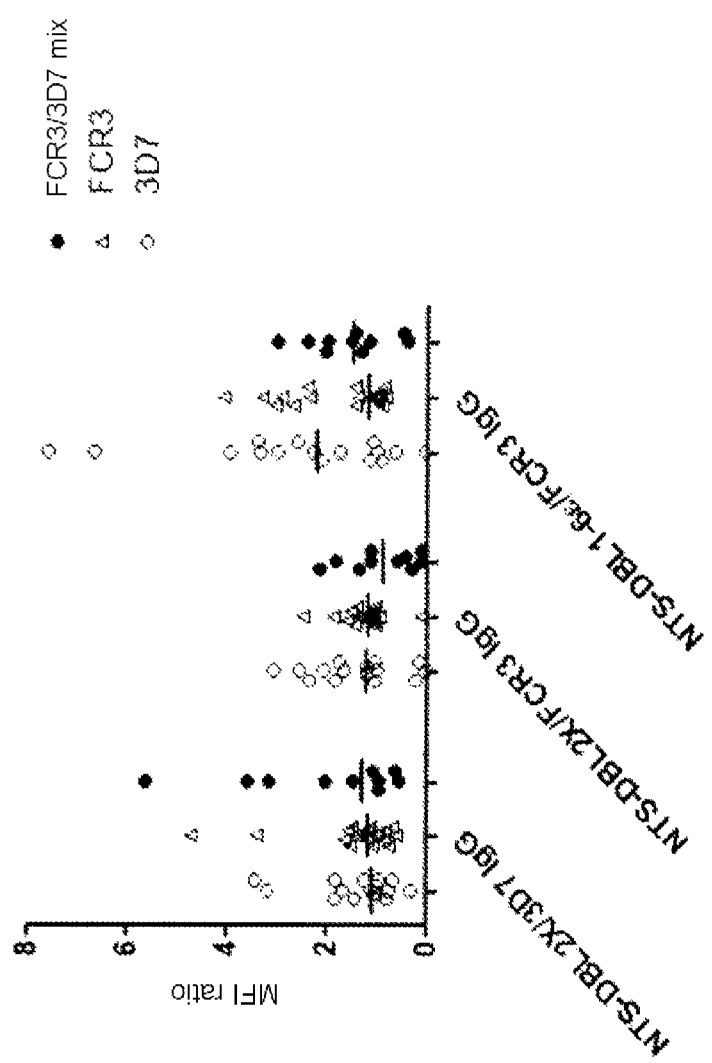

FIG. 2 is a graph showing the recognition of VAR2CSA expressed in field isolates by the IgGs directed against the various constructs of Var2CSA. The capacity for recognition of VAR2CSA expressed by the IgGs induced against the constructs of VAR2CSA (NTS-DBL2X/3D7 and NTS-DBL2X/FCR3) and against the entire extracellular domain of VAR2CSA (NTS-DBL1-6e/FCR3) of the FCR3 strain was studied on field isolates by flow cytometry. The parasites were separated as a function of their DSM category (DSM 3D7, DSM FCR3 or DSM Mixture FCR3/3D7). The bars indicate mean value of the MFI ratio (MFI corresponding to the reactivity of the IgG of the hyper-immune animal/MFI corresponding to the reactivity of the IgG of the same animal pre-immunization.

Figure 3:
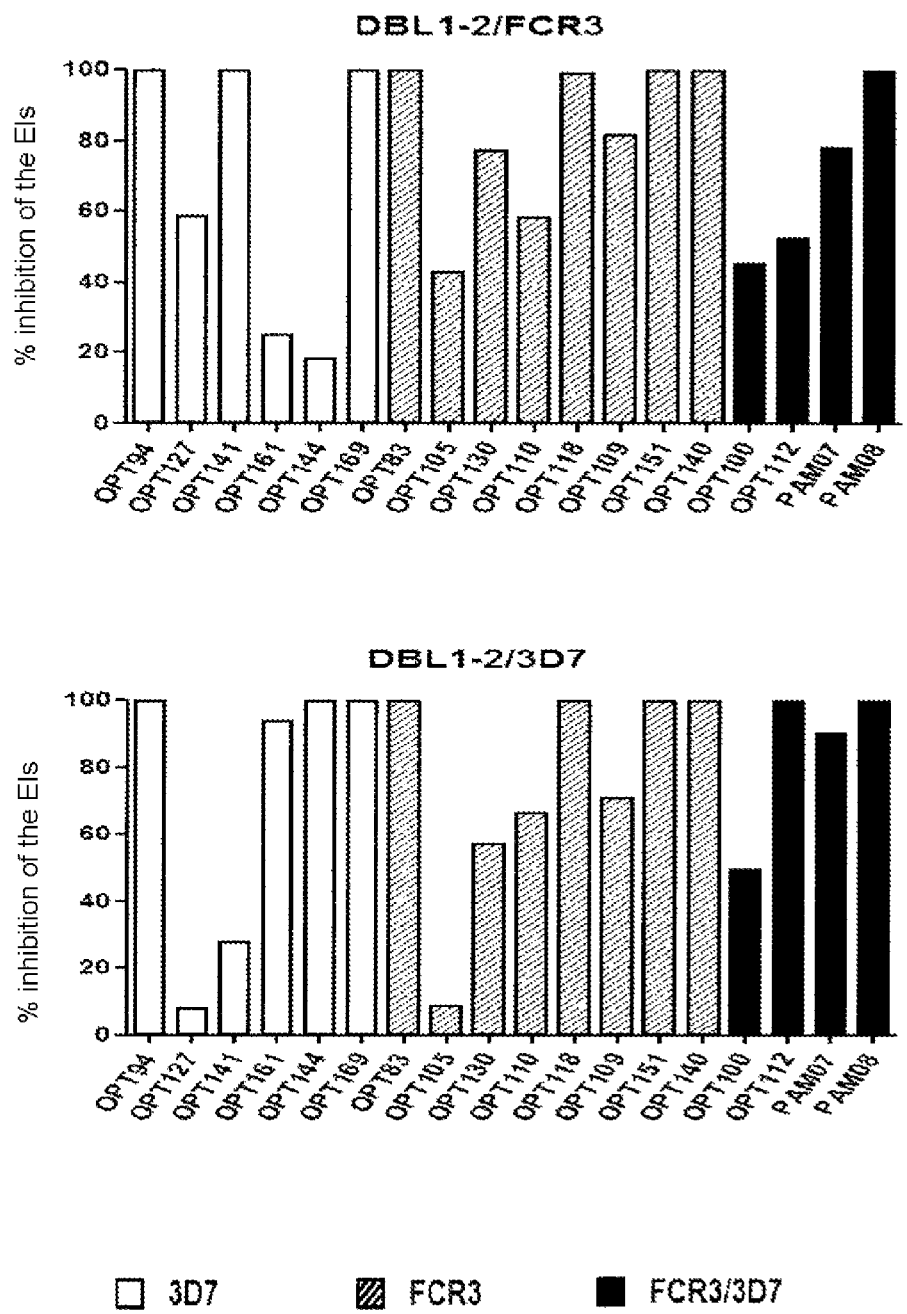

FIG. 3 comprises two graphs showing the adhesion inhibiting activity of IgG induced against each of the two 'serotypes' of NTS-DBL1x-Id1-DBL2x on field isolates. The adhesion inhibiting activity was evaluated on 18 *Plasmodium falciparum* isolates freshly obtained from pregnant women. The data are presented in the form of percentage inhibition for each antibody normalized by the value of inhibition of CSA (used as a reference of maximum inhibition of adhesion). The histograms are presented for each of the types of DSM detected in the isolate: ☐ for the DSMs of type 3D7, ▨ for the DSMs of type FCR3, and ■ for the DSMs of a mixture of the two genotypes.

Figure 4:
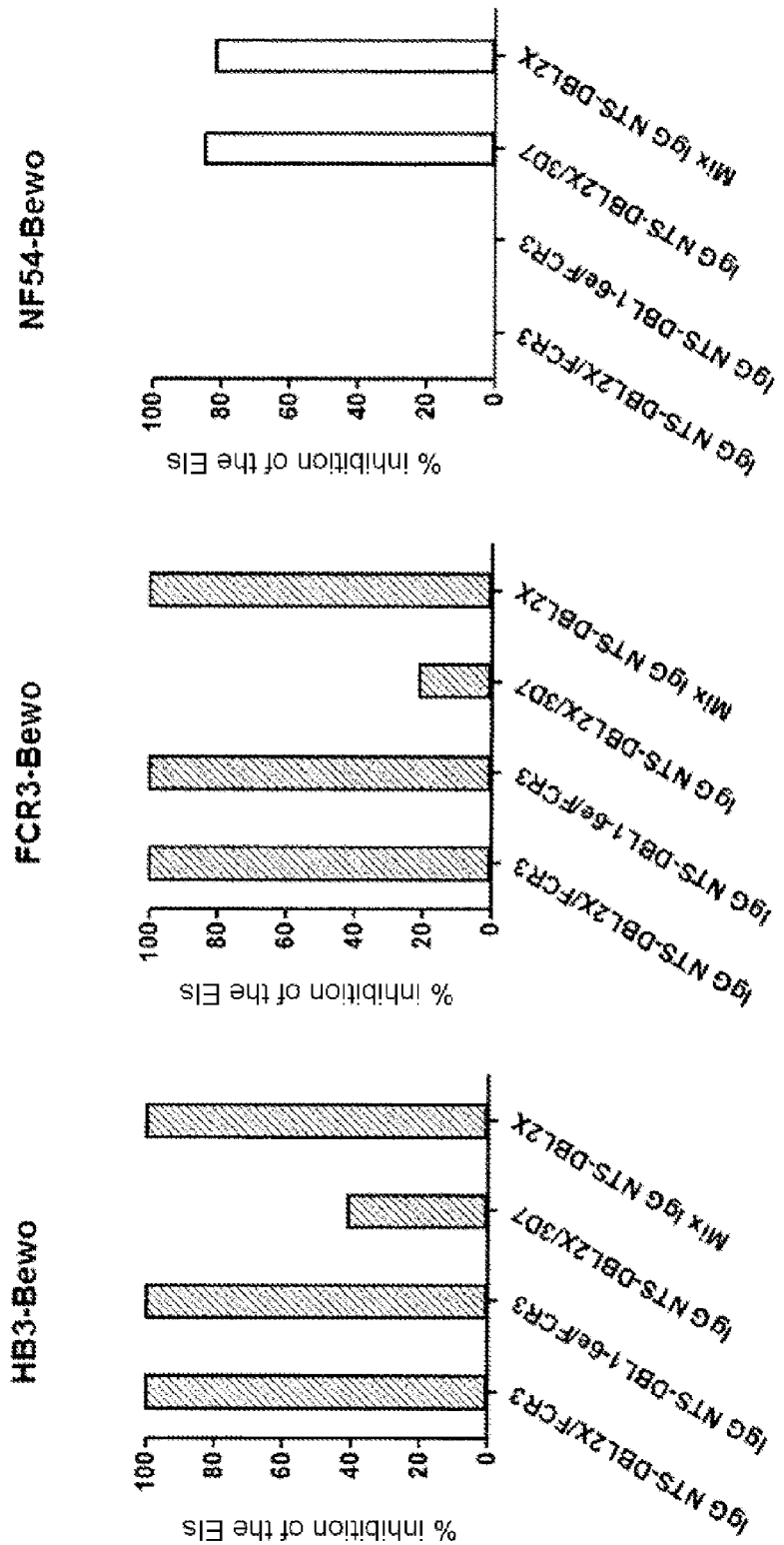

FIG. 4 is a series of three graphs showing the inhibition profile of the antibodies on selected and adapted strains that bind to CSA. The strains FCR3, HB3 and NF54 selected on Bewo cells (FCR3-Bewo, HB36-Bewo and NF54-Bewo) were used for evaluating the capacity of the induced antibodies for inhibiting the adherence of the 3 laboratory strains to CSPG. The in vitro functionality of the mixtures of antibodies was also evaluated. The values presented are normalized with the value for inhibition of CSA.

Figure 5:
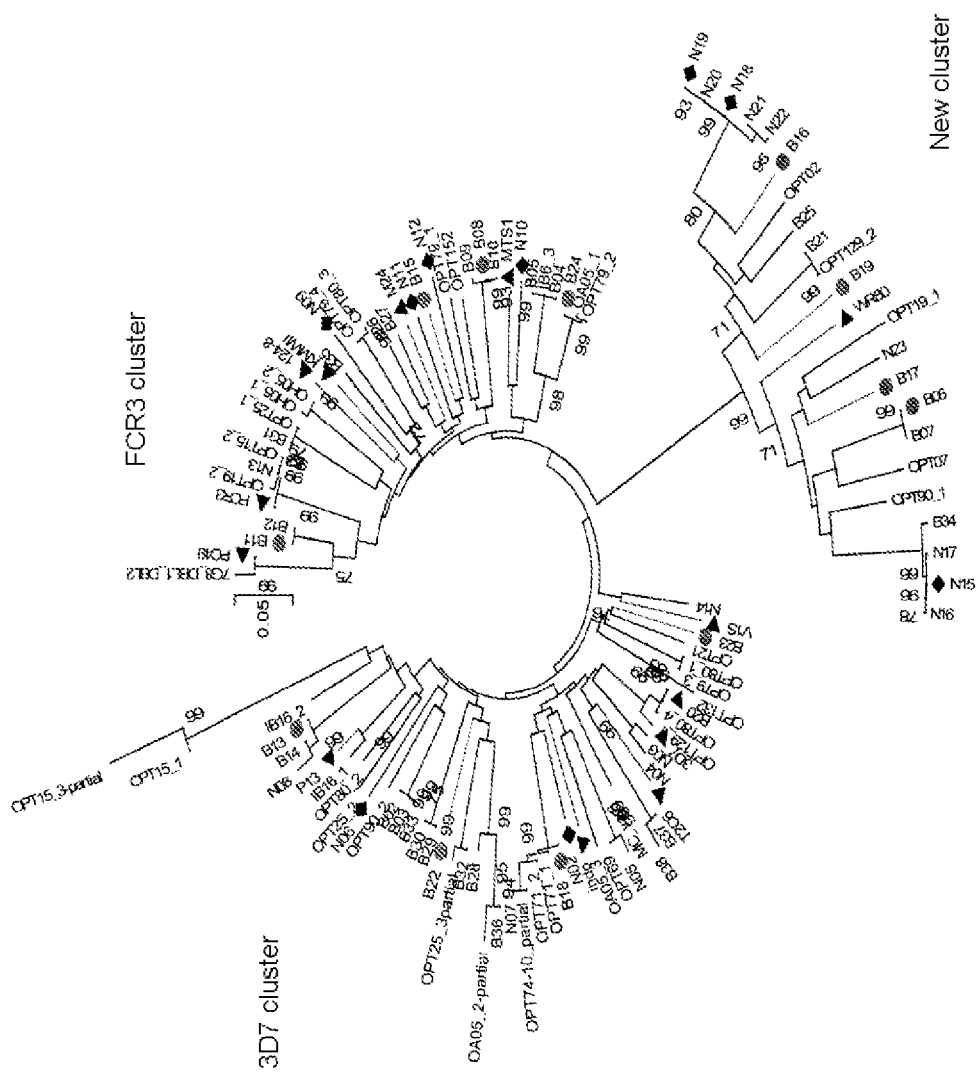

FIG. 5 is a representation of the phylogenetic relations between the sequences covering the region ID1-DBL2X of VAR2CSA generated from the cDNA of 123 parasitic isolates from pregnant women. The phylogenetic tree illustrates the phylogenetic relation between the different sequences, with the groupings of the dichotomic variants defined in the DBL2X that discriminates the clusters 3D7 and FCR3 and the groupings of a new cluster whose identity is defined in the Id1 region of VAR2CSA. The bootstrap values are indicated at each principal bifurcation.

RESULTS

Determination of the Multiplicity of Infection and Molecular Typing of var2csa Among the Parasites Isolated from Pregnant Women In total, 122 parasites were collected, and it was determined by genotyping of msp-2 that the multiplicity of infection (MOI) is 3.10 distinct genotypes per isolate with a range from 1 to 7. A PCR-RFLP method was developed and implemented on all the isolates to study the distribution of the two major variants of var2csa among the field isolates from Benin. Analysis of the dimorphic region of var2csa in the isolates from pregnant women revealed the presence of at least one of the two dimorphic variants described by Sander et al. (PLoS One, 2009, 4: e6667) in all the parasites. The transcripts of DSM of type 3D7 were found in 54 isolates (44%) and the transcripts of DSM of type FCR3 were found in 47 isolates (39%) (FIG. 1). In 21 isolates (17%), both types of transcripts were detected, suggesting a mixture of genotypes. No difference was observed between the MOI values of the isolates of the groups determined after typing of var2csa (the MOI values determined are 3.05 in the isolates expressing type 3D7, 2.98 in the isolates expressing type CFR3 and 3.6 in the isolates with a mixture of both DSM signatures).

IgG Specifically Induced Against the NTS-DBL1x-Id1-DBL2x Region of the FCR3 and 3D7 Lines Recognize all the Isolates from Pregnant Women The recognition level of VAR2SCA expressed on the surface of the erythrocytes was estimated immunologically on 47 erythrocytes infected by *Plasmodium falciparum* isolated from pregnant women. Among these isolates, it was found that 16 of them have the DSM of type 3D7, 21 have the DSM of type FCR3 and a mixture of genotypes was detected in 10 isolates. The infected erythrocytes were labeled and evaluated by flow cytometry using purified IgGs from sera of vaccinated animals. The anti-NTS-DBL1x-Id1-DBL2x IgGs specific to the var2csa variants of 3D7 and FCR3, and the IgGs induced against the entire extracellular domain of VAR2CSA were used in this experiment. The IgGs induced against the entire extracellular domain of VAR2CSA were used for estimating the absolute recognition level of the native VAR2CSA protein expressed on the surface of the infected erythrocytes. A high level of reactivity was observed with antibodies induced against the entire extracellular domain of VAR2CSA compared to the antibodies directed against the NTS-DBL1x-Id1-DBL2x domain of VAR2CSA whatever the origin of the latter (P<0.05). However, no significant difference was observed between the recognition levels of the VAR2CSA native protein by the anti-NTS-DBL1x-Id1-DBL2x IgGs induced against the FCR3 variant and against the 3D7 variant (P=0.59). The inventors then investigated whether the surface recognition of the antibodies was influenced by the genotype of var2csa. The isolates were divided up as a function of the type of DSM of their var2csa. The data of the infected erythrocytes labeled by each antibody were separated as a function of the DSM of the isolates. No significant difference was observed at the level of recognition of VAR2CSA by each antibody tested whatever the type of DSM (FIG. 2).

Adhesion Inhibition Properties of the Anti-NTS-DBL1x-Id1-DBL2x IgGs Specific of the FCR3 and 3D7 Variants.

Analysis of the inhibitory activity of the antibodies was also performed on 18 samples of infected erythrocytes binding to CSA obtained from pregnant women in Benin. Typing of the DSMs of these isolates revealed that 6 of them (33%) express the DSM of type 3D7 of var2csa; 8 (44%) express the DSM of type FCR3 of var2csa; and 4 (22%) are mixtures of the two types (FIG. 3).

Soluble CSA was used as reference of maximum inhibition of adhesion. The degree of inhibition of the parasites by the anti-NTS-DBL1x-Id1-DBL2x antibodies of the FCR3 and 3D7 variants was normalized to the inhibition of CSA. The mean value of the inhibitory activity of the antibodies on all the isolates is 80% [interquartile range: 50.8-100] for the anti-NTS-DBL1x-Id1-DBL2x antibody of the FCR3 variant and 97% [interquartile range: 55.3-100] for the anti-NTS-DBL1x-Id1-DBL2x antibody of the 3D7 variant. Different modes of inhibition were observed with the antibodies depending on the types of var2csa of the isolates. 16 of the 18 isolates tested (89%) were effectively inhibited by the antibodies induced against the NTS-DBL1x-Id1-DBL2x domain of the FCR3 variant (43-100%) whereas a strong inhibitory activity of the antibodies induced against the NTS-DBL1x-Id1-DBL2x domain of the 3D7 variant (50-100%) was observed on 15 of the 18 isolates (84% tested). However, it appears that the activities of the two types of antibodies on the various isolates tested differ from one another. The inhibitory effect of one of the two types of antibodies may be weak in one isolate whereas the antibodies induced against the other serotype may have a strong inhibitory effect on the same parasite. For example, the isolates OPT144 and OPT161 are not inhibited by the antibodies induced against the FCR3 serotype, and interestingly, these isolates bearing the DSM of type 3D7 were strongly inhibited by the specific IgGs of the NTS-DBL1x-Id1-DBL2x domain of the 3D7 variant. A similar profile was obtained with the isolate OPT105, which is more strongly inhibited with the specific IgGs of the homologous DSM serotype of the FCR3 variant and less well inhibited with the anti-NTS-DBL1x-Id1-DBL2x IgGs specific to the 3D7 variant. Conversely, in two isolates with 3D7 serotypes (OPT127 and OPT141), better inhibition was observed with antibodies induced against the opposite FCR3 serotype. Generally, complementarity of inhibition was observed on the field isolates, with a substantial increase in the extent of inhibition of adherence of the field isolates to CSPG, now reaching 100% of the isolates currently inhibited. Moreover, 8 of the 10 isolates (80%) with a DSM of type 3D7 of var2csa were inhibited with anti-NTS-DBL1x-Id1-DBL2x antibodies induced against the homologous DSM variant whereas all the isolates with the DSM of type FCR3 of var2csa were effectively inhibited by the anti-NTS-DBL1x-Id1-DBL2x IgGs specific to the FCR3 serotype.

The capacity of the antibodies for inhibiting adherence of infected erythrocytes expressing VAR2CSA to CSA and the behavior of the mixture of the two antibodies induced against the NTS-DBL1x-Id1-DBL2x domain of VAR2CSA were studied on the laboratory strains and strains selected by Bewo: FCR3 and HB3 (which have a DSM of type FCR3) and NF54 (which has a background of type 3D7). High inhibitory activity was obtained with antibodies to infected erythrocytes belonging to the homologous DSM. The anti-NTS-DBL1x-Id1-DBL2x antibodies induced against the FCR3 variant completely (100%) inhibit the adherence of the FCR23 and HB3 lines to CSA (FIG. 4). However, only partial inhibition of these lines (20% to 40%) was observed with the anti-NTS-DBL1x-Id1-DBL2x IgGs induced against the 3D7 variant, which moreover strongly inhibit the adherence of the NF54 parasite to CSA. Moreover, the mixture of the anti-NTS-DBL1x-Id1-DBL2x IgGs of the FCR3 line and of the 3D7 line conserve the property of completely inhibiting the adherence of all the infected erythrocytes to CSPG.

Identification of a Third Cluster.

The sequence variations of the NTS-DBL1x-Id1-DBL2x domain of the VAR2CSA protein of the transcript of 123 parasitic isolates from pregnant women in Benin were analyzed. The total RNA was extracted from the freshly collected parasites, and the cDNA was synthesized. The var2csa gene was amplified from the cDNA using a high-fidelity enzyme (Fusion), and universal primers were used. Ten (10) clones were sequenced for each isolate and the sequences were generated by multiple alignment of the protein and nucleic acid sequences.

The results of the analyses clearly demonstrated segregation of the parasitic variants in the Id1 region of VAR2CSA. This new dichotomy domain, which has not been described hitherto, is located in a critical region of the VAR2CSA protein that is essential for its CSA binding properties. This very clean segregation of the sequences will have implications in the combination of a limited number of variants required for an optimal vaccine based on VAR2CSA.

The sequence alignments led to the establishment of two consensus sequences representative of the Id1 interdomain of VAR2CSA. The first, ID1A or SEQ ID NO: 11 corresponds to the recently identified cluster, and the second, ID1B or SEQ ID NO: 12 corresponds to the other group of sequences.

CONCLUSIONS

This work demonstrates that the NTS-DBL2X region of VAR2CSA contains conserved anti-adherence epitopes and indicates that the development of an effective vaccine based on VAR2CSA will require combination of a restricted number of VAR2CSA variants. The combination of the three major variants of VAR2CSA used in this work will be essential for developing an effective vaccine against placental malaria.

The invention claimed is:

1. An immunogenic composition comprising a combination of at least two isolated or purified polypeptides,
    wherein the first isolated or purified polypeptide consists of the NTS-DBL1x-Id1-DBL2x region or the Id1-DBL2x region of the VAR2CSA protein of a first parasitic family of *Plasmodium falciparum* whose VAR2CSA protein is characterized by an Id1 interdomain that has as sequence the consensus sequence SEQ ID NO: 11 or that is encoded by the consensus sequence SEQ ID NO: 13; and
    the second isolated or purified polypeptide consists of the NTS-DBL1x-Id1-DBL2x region or the Id1-DBL2x region of the VAR2CSA protein of a second parasitic family of *Plasmodium falciparum* whose VAR2CSA protein is characterized by an Id1 interdomain that has as sequence the consensus sequence SEQ ID NO: 12 or that is encoded by the consensus sequence SEQ ID NO: 14, and
    wherein each of the isolated or purified polypeptides is fused to a fusion partner sequence, thus forming a fusion protein.

2. The immunogenic composition according to claim 1, wherein the second parasitic family of *Plasmodium falciparum* comprises the parasitic line FCR3 and the parasitic line 3D7.

3. The immunogenic composition according to claim 2, wherein said immunogenic composition comprises three isolated or purified polypeptides,
    wherein the first isolated or purified polypeptide consists of the NTS-DBL1x-Id1-DBL2x region or the Id1-DBL2x region of the VAR2CSA protein of the parasitic family of *Plasmodium falciparum* whose VAR2CSA protein is characterized by an Id1 interdomain having as sequence the consensus sequence SEQ ID NO: 11,
    the second isolated or purified polypeptide consists of the NTS-DBL1x-Id1-DBL2x region or the Id1-DBL2x region of the VAR2CSA protein of the FCR3 line, and
    the third isolated or purified polypeptide consists of the NTS-DBL1x-Id1-DBL2x region or the Id1-DBL2x region of the VAR2CSA protein of the 3D7 line.

4. The immunogenic composition according to claim 3, wherein the NTS-DBL1x-Id1-DBL2x region of the VAR2CSA protein of the FCR3 line has the sequence SEQ ID NO: 1 or a homologous sequence of SEQ ID NO: 1,
    the Id1-DBL2x region of the VAR2CSA protein of the FCR3 line has the sequence SEQ ID NO: 3 or a homologous sequence of SEQ ID NO: 3,
    the NTS-DBL1x-Id1-DBL2x region of the VAR2CSA protein of the 3D7 line has the sequence SEQ ID NO: 5 or a homologous sequence of SEQ ID NO: 5, and
    the Id1-DBL2x region of the VAR2CSA protein of the 3D7 line has the sequence SEQ ID NO: 7 or a homologous sequence of SEQ ID NO: 7.

5. The immunogenic composition according to claim 1, wherein each of the fusion partner sequences is selected independently from the group consisting of the maltose-binding protein, the signal sequence of the maltose-binding protein, an S-tag, glutathione-S-transferase, thioredoxin, β-galactosidase, streptavidin, dihydrofolate reductase, the signal sequence pelB, the signal sequence ompA, the signal sequence of alkaline phosphatase, green fluorescent protein, toxins, human growth hormone, interleukin-2 (IL-2), granulocyte macrophage colony stimulating factor (GM-CSF), granulocyte colony stimulating factor (G-CSF), calcitonin, interferon beta, interferon alfa, glucagon-like peptide 1 (GLP-1), glucagon-like peptide 2 (GLP-2), toxin PA, the parathyroid hormones (PTH(1-34) and PTH(1-84)), butyrylcholinesterase, glucocerebrosidase (GB A), and exendin-4.

6. The immunogenic composition according to claim 1 further comprising at least one pharmaceutically acceptable vehicle or excipient or at least one adjuvant.

7. The immunogenic composition according to claim 3, wherein each of the fusion partner sequences is selected from the group consisting of:
    a maltose-binding protein, the signal sequence of the maltose-binding protein, an S-tag, glutathione-S-transferase, thioredoxin, β-galactosidase, streptavidin, dihydrofolate reductase, the signal sequence pelB, the signal sequence ompA, the signal sequence of alkaline phosphatase, green fluorescent protein, toxins, human growth hormone, interleukin-2 (IL-2), granulocyte macrophage colony stimulating factor (GM-CSF), granulocyte colony stimulating factor (G-CSF), calcitonin, interferon beta, interferon alfa, glucagon-like peptide 1 (GLP-1), glucagon-like peptide 2 (GLP-2), toxin PA, the parathyroid hormones (PTH(1-34) and PTH(1-84)), butyrylcholinesterase, glucocerebrosidase (GBA), and exendin-4.

8. The immunogenic composition according to claim 3 further comprising at least one pharmaceutically acceptable vehicle or excipient or at least one adjuvant.

9. The immunogenic composition according to claim 4, wherein each of the fusion partner sequences is selected from the group consisting of:
    a maltose-binding protein, the signal sequence of the maltose-binding protein, an S-tag, glutathione-S-transferase, thioredoxin, β-galactosidase, streptavidin, dihydrofolate reductase, the signal sequence pelB, the signal sequence ompA, the signal sequence of alkaline phosphatase, green fluorescent protein, toxins, human growth hormone, interleukin-2 (IL-2), granulocyte macrophage colony stimulating factor (GM-CSF), granulocyte colony stimulating factor (G-CSF), calcitonin, interferon beta, interferon alfa, glucagon-like peptide 1 (GLP-1), glucagon-like peptide 2 (GLP-2), toxin PA, the parathyroid hormones (PTH(1-34) and PTH(1-84)), butyrylcholinesterase, glucocerebrosidase (GBA), and exendin-4.

10. The immunogenic composition according to claim 4 further comprising at least one pharmaceutically acceptable vehicle or excipient or at least one adjuvant.

11. A kit comprising the immunogenic composition according to claim 1, and instructions for inducing a protective immune response against *Plasmodium falciparum* in a female human being.

* * * * *

SEQUENCE LISTING

<160> NUMBER OF SEQ ID NOS: 14

<210> SEQ ID NO 1
<211> LENGTH: 869
<212> TYPE: PRT
<213> ORGANISM: Plasmodium falciparum -continued

```
<400> SEQUENCE: 1

Asn Lys Ile Glu Glu Tyr Leu Gly Ala Lys Ser Asp Ser Lys Ile
1               5                   10                  15

Asp Glu Leu Leu Lys Ala Asp Pro Ser Glu Val Glu Tyr Tyr Arg Ser
            20                  25                  30

Gly Gly Asp Gly Asp Tyr Leu Lys Asn Asn Ile Cys Lys Ile Thr Val
                35                  40                  45

Asn His Ser Asp Ser Gly Lys Tyr Asp Pro Cys Glu Lys Lys Leu Pro
        50                  55                  60

Pro Tyr Asp Asp Asn Asp Gln Trp Lys Cys Gln Gln Asn Ser Ser Asp
65                  70                  75                  80

Gly Ser Gly Lys Pro Glu Asn Ile Cys Val Pro Pro Arg Arg Glu Arg
                85                  90                  95

Leu Cys Thr Tyr Asn Leu Glu Asn Leu Lys Phe Asp Lys Ile Arg Asp
                100                 105                 110

Asn Asn Ala Phe Leu Ala Asp Val Leu Leu Thr Ala Arg Asn Glu Gly
                115                 120                 125

Glu Lys Ile Val Gln Asn His Pro Asp Thr Asn Ser Ser Asn Val Cys
    130                 135                 140

Asn Ala Leu Glu Arg Ser Phe Ala Asp Leu Ala Asp Ile Ile Arg Gly
145                 150                 155                 160

Thr Asp Gln Trp Lys Gly Thr Asn Ser Asn Leu Glu Lys Asn Leu Lys
                165                 170                 175

Gln Met Glu Thr Phe Ala Lys Ile Arg Glu Asn Asp Lys Val Leu Gln
                180                 185                 190

Asp Lys Tyr Pro Lys Asp Gln Lys Tyr Thr Lys Leu Arg Glu Ala Trp
            195                 200                 205

Trp Asn Ala Asn Arg Gln Lys Val Trp Glu Val Ile Thr Cys Gly Ala
210                 215                 220

Arg Ser Asn Asp Leu Leu Ile Lys Arg Gly Trp Arg Thr Ser Gly Lys
225                 230                 235                 240

Ser Asp Arg Lys Lys Asn Phe Glu Leu Cys Arg Lys Cys Gly His Tyr
                245                 250                 255

Glu Lys Glu Val Pro Thr Lys Leu Asp Tyr Val Pro Gln Phe Leu Arg
                260                 265                 270

Trp Leu Thr Glu Trp Ile Glu Asp Phe Tyr Arg Glu Lys Gln Asn Leu
            275                 280                 285

Ile Asp Asp Met Glu Thr Glu Arg His Arg Glu Glu Cys Thr Arg Glu
290                 295                 300

Asp His Lys Ser Lys Glu Gly Thr Ser Tyr Cys Ser Thr Cys Lys Asp
305                 310                 315                 320

Lys Cys Lys Lys Tyr Cys Glu Cys Val Lys Lys Trp Lys Thr Glu Trp
                325                 330                 335

Glu Asn Gln Glu Asn Lys Tyr Lys Asp Leu Tyr Glu Gln Asn Lys Asn
            340                 345                 350

Lys Thr Ser Gln Lys Asn Thr Ser Arg Tyr Asp Asp Tyr Val Lys Asp
        355                 360                 365

Phe Phe Glu Lys Leu Glu Ala Asn Tyr Ser Ser Leu Glu Asn Tyr Ile
370                 375                 380

Lys Gly Asp Pro Tyr Phe Ala Glu Tyr Ala Thr Lys Leu Ser Phe Ile
385                 390                 395                 400

Leu Asn Pro Ser Asp Ala Asn Asn Pro Ser Gly Glu Thr Ala Asn His
                405                 410                 415
```

-continued

```
Asn Asp Glu Ala Cys Asn Cys Asn Glu Ser Gly Ile Ser Ser Val Gly
                420                 425                 430
Gln Ala Gln Thr Ser Gly Pro Ser Ser Asn Lys Thr Cys Ile Thr His
            435                 440                 445
Ser Ser Ile Lys Thr Asn Lys Lys Glu Cys Lys Asp Val Lys Leu
450                 455                 460
Gly Val Arg Glu Asn Asp Lys Asp Leu Lys Ile Cys Val Ile Glu Asp
465                 470                 475                 480
Thr Ser Leu Ser Gly Val Asp Asn Cys Cys Gln Asp Leu Leu Gly
                485                 490                 495
Ile Leu Gln Glu Asn Cys Ser Asp Asn Lys Arg Gly Ser Ser Ser Asn
                500                 505                 510
Asp Ser Cys Asp Asn Lys Asn Gln Asp Glu Cys Gln Lys Lys Leu Glu
                515                 520                 525
Lys Val Phe Ala Ser Leu Thr Asn Gly Tyr Lys Cys Asp Lys Cys Lys
                530                 535                 540
Ser Gly Thr Ser Arg Ser Lys Lys Lys Trp Ile Trp Lys Lys Ser Ser
545                 550                 555                 560
Gly Asn Glu Glu Gly Leu Gln Glu Glu Tyr Ala Asn Thr Ile Gly Leu
                565                 570                 575
Pro Pro Arg Thr Gln Ser Leu Tyr Leu Gly Asn Leu Pro Lys Leu Glu
            580                 585                 590
Asn Val Cys Glu Asp Val Lys Asp Ile Asn Phe Asp Thr Lys Glu Lys
            595                 600                 605
Phe Leu Ala Gly Cys Leu Ile Val Ser Phe His Glu Gly Lys Asn Leu
610                 615                 620
Lys Lys Arg Tyr Pro Gln Asn Lys Asn Ser Gly Asn Lys Glu Asn Leu
625                 630                 635                 640
Cys Lys Ala Leu Glu Tyr Ser Phe Ala Asp Tyr Gly Asp Leu Ile Lys
                645                 650                 655
Gly Thr Ser Ile Trp Asp Asn Glu Tyr Thr Lys Asp Leu Glu Leu Asn
                660                 665                 670
Leu Gln Asn Asn Phe Gly Lys Leu Phe Gly Lys Tyr Ile Lys Lys Asn
                675                 680                 685
Asn Thr Ala Glu Gln Asp Thr Ser Tyr Ser Ser Leu Asp Glu Leu Arg
690                 695                 700
Glu Ser Trp Trp Asn Thr Asn Lys Lys Tyr Ile Trp Thr Ala Met Glu
705                 710                 715                 720
Thr Lys His Gly Ala Glu Met Glu Thr Asn Ile Thr Thr Cys Asn Ala
                725                 730                 735
Asp Gly Ser Val Thr Gly Ser Gly Ser Cys Asp Asp Ile Pro Thr
                740                 745                 750
Ile Asp Leu Ile Pro Gln Tyr Leu Arg Phe Leu Gln Glu Trp Val Glu
                755                 760                 765
Asn Phe Cys Glu Gln Arg Gln Ala Lys Val Lys Asp Val Ile Thr Asn
            770                 775                 780
Cys Lys Ser Cys Lys Glu Ser Gly Asn Lys Cys Lys Thr Glu Cys Lys
785                 790                 795                 800
Thr Lys Cys Lys Asp Glu Cys Glu Lys Tyr Lys Lys Phe Ile Glu Ala
                805                 810                 815
Cys Gly Thr Ala Gly Gly Gly Ile Gly Thr Ala Gly Ser Pro Trp Ser
                820                 825                 830
```

| Lys | Arg | Trp | Asp | Gln | Ile | Tyr | Lys | Arg | Tyr | Ser | Lys | His | Ile | Glu | Asp |
|---|---|---|---|---|---|---|---|---|---|---|---|---|---|---|---|
| 835 | | | | | 840 | | | | | 845 | | | | | |

| Ala | Lys | Arg | Asn | Arg | Lys | Ala | Gly | Thr | Lys | Asn | Cys | Gly | Thr | Ser | Ser |
|---|---|---|---|---|---|---|---|---|---|---|---|---|---|---|---|
| 850 | | | | | 855 | | | | | 860 | | | | | |

| Thr | Thr | Asn | Ala | Ala |
|---|---|---|---|---|
| 865 | | | | |

<210> SEQ ID NO 2
<211> LENGTH: 2583
<212> TYPE: DNA
<213> ORGANISM: Plasmodium falciparum

<400> SEQUENCE: 2

```
aacaaaattg aagaatattt aggtgcaaaa tccgatgatt ctaaaataga cgaattgttg      60
aaagctgatc ctagtgaagt ggaatactat agaagtggag gtgatggaga ttacttaaaa     120
aataatattt gtaaaattac cgtgaatcat tcagattctg gaaagtatga tccttgtgag     180
aaaaaattac ctccttatga tgataatgac caatggaaat gtcagcaaaa ttcatctgat     240
ggaagtggaa aacctgaaaa tatatgtgtc cctccgagaa gagaaagatt atgtacgtat     300
aatttagaaa acttaaaatt tgataaaatt agggataata atgcattttt ggctgatgta     360
ttacttacag ctagaaatga aggagaaaaa atagtgcaga atcatccaga tacaaatagt     420
tccaatgttt gtaatgcttt agaaagaagt tttgctgatc ttgcagatat tattagaggt     480
acagatcaat ggaaaggtac taatagtaat ttagaaaaaa atttaaaaca aatgtttgca     540
aaaatacgag aaaacgacaa ggtacttcaa gataaatacc caaggaccaa aaatatataca    600
aaattacgag aagcttggtg gaatgctaat agacaaaagg tgtgggaagt tattacttgc     660
ggtgcacgaa gtaacgattt actcataaaa cgtggatgga aacatctgg aaaatctgat      720
agaaaaaaga acttcgaatt gtgccgcaaa tgtggccatt atgaaaaaga ggttcctacc     780
aaattagatt atgtccctca attcttaagg tggttaacag aatggataga ggattttat      840
agagagaagc aaaatctgat cgatgacatg gagaggcacc gtgaagagtg tacaagagag     900
gatcataaat ctaaagaagg tacatcatat tgtagtacct gtaaagacaa atgtaagaaa     960
tattgtgaat gtgtgaagaa atggaagacc gaatgggaaa atcaagaaaa taatataaaa    1020
gatttatatg aacaaaacaa aaacaaaact tcgcaaaaaa atacatcaag atatgatgat    1080
tatgttaaag attttttttga aaaacttgaa gctaattatt cgtctcttga aaattatata   1140
aagggtgatc cttatttcgc agaatatgca accaaattat catttatttt aaatccatca    1200
gatgctaata tccgtctgg agaaacagca aaccataatg atgaagcatg taactgtaat    1260
gaatcaggaa tttcatcagt tggacaggca caaacatcgg gtccgtcgtc gaataaaaca    1320
tgtatcacac atagctctat aaaaactaat aagaaaaaag aatgtaaaga tgtaaagttg    1380
ggtgttcgtg aaaatgataa agatttgaaa atatgcgtaa ttgaggacac ttccttaagt    1440
ggtgttgata attgttgttg ccaagattta ttgggaattc ttcaagaaaa ttgtagtgat    1500
aataaacgtg gatctagttc taatgatagt tgtgataaca aaaatcagga tgaatgtcaa    1560
aagaaattag aaaagtatt tgcatctta acgaatggtt ataaatgcga caatgtaaa      1620
tctggaacat caagaagtaa aaaaaaatgg atatggaaaa atcctctgg taatgaagaa    1680
ggattacaag aagaatatgc taacaccata ggtttacccc caagaacaca atcgttatat    1740
ttaggaaatc tacctaaact tgaaaatgtg tgcgaagatg taaggatat taattttgat   1800
acaaaagaga aatttctagc aggatgctta attgtttctt ttcatgaagg aaaaaattta    1860
```

```
aaaaaaagat accctcaaaa taaaaattct ggaaataaag aaaatttatg caaagctttta    1920 gaatatagtt ttgctgatta tggagattta attaaaggta caagtatatg ggataatgaa    1980
tatacaaaag atctggaact aaatttacaa aacaattttg gaaaacttttt tggtaaatat   2040 ataaaaaaga ataataccgc tgaacaagat acttcatatt cttctcttga tgaattaaga    2100
gaatcatggt ggaacacgaa caaaaaatat atttggacag caatgaaaca tggtgcagaa    2160
atgaatatta ctacgtgtaa tgctgatggt agtgtcactg gtagtggtag tagttgtgat    2220
gatattccta cgattgattt gatcccgcaa tatttacgtt ttttgcaaga atgggtagaa    2280 aattttttgcg aacaacgtca agcaaaagta aagatgtgta taacgaactg taagtcgtgt   2340
aaggaaagtg gaaacaaatg taaaactgaa tgtaaaacaa aatgtaaaga cgagtgtgaa    2400
aaatacaaaa aatttattga agcgtgtggt acagctggtg gtggtattgg tactgctgga    2460
tctccatgga gcaaaggtg ggaccaaata tataagaggt attccaaaca tatagaagac     2520
gcgaaacgaa accgtaaagc gggcacaaaa aattgtggta caagtagtac tacaaatgct   2580
gcc                                                                   2583

<210> SEQ ID NO 3
<211> LENGTH: 482
<212> TYPE: PRT
<213> ORGANISM: Plasmodium falciparum

<400> SEQUENCE: 3

Pro Tyr Phe Ala Glu Tyr Ala Thr Lys Leu Ser Phe Ile Leu Asn Pro
1               5                   10                  15

Ser Asp Ala Asn Asn Pro Ser Gly Glu Thr Ala Asn His Asn Asp Glu
            20                  25                  30

Ala Cys Asn Cys Asn Glu Ser Gly Ile Ser Ser Val Gly Gln Ala Gln
        35                  40                  45

Thr Ser Gly Pro Ser Ser Asn Lys Thr Cys Ile Thr His Ser Ser Ile
    50                  55                  60

Lys Thr Asn Lys Lys Lys Glu Cys Lys Asp Val Lys Leu Gly Val Arg
65                  70                  75                  80

Glu Asn Asp Lys Asp Leu Lys Ile Cys Val Ile Glu Asp Thr Ser Leu
                85                  90                  95

Ser Gly Val Asp Asn Cys Cys Cys Gln Asp Leu Leu Gly Ile Leu Gln
            100                 105                 110

Glu Asn Cys Ser Asp Asn Lys Arg Gly Ser Ser Ser Asn Asp Ser Cys
        115                 120                 125

Asp Asn Lys Asn Gln Asp Glu Cys Gln Lys Lys Leu Glu Lys Val Phe
    130                 135                 140

Ala Ser Leu Thr Asn Gly Tyr Lys Cys Asp Lys Cys Lys Ser Gly Thr
145                 150                 155                 160

Ser Arg Ser Lys Lys Lys Trp Ile Trp Lys Ser Ser Gly Asn Glu
                165                 170                 175

Glu Gly Leu Gln Glu Glu Tyr Ala Asn Thr Ile Gly Leu Pro Pro Arg
            180                 185                 190

Thr Gln Ser Leu Tyr Leu Gly Asn Leu Pro Lys Leu Glu Asn Val Cys
        195                 200                 205

Glu Asp Val Lys Asp Ile Asn Phe Asp Thr Lys Glu Lys Phe Leu Ala
    210                 215                 220

Gly Cys Leu Ile Val Ser Phe His Glu Gly Lys Asn Leu Lys Lys Arg
225                 230                 235                 240
```

Tyr Pro Gln Asn Lys Asn Ser Gly Asn Lys Glu Asn Leu Cys Lys Ala
            245                 250                 255

Leu Glu Tyr Ser Phe Ala Asp Tyr Gly Asp Leu Ile Lys Gly Thr Ser
        260                 265                 270

Ile Trp Asp Asn Glu Tyr Thr Lys Asp Leu Glu Leu Asn Leu Gln Asn
            275                 280                 285

Asn Phe Gly Lys Leu Phe Gly Lys Tyr Ile Lys Lys Asn Asn Thr Ala
        290                 295                 300

Glu Gln Asp Thr Ser Tyr Ser Ser Leu Asp Glu Leu Arg Glu Ser Trp
305                 310                 315                 320

Trp Asn Thr Asn Lys Lys Tyr Ile Trp Thr Ala Met Glu Thr Lys His
            325                 330                 335

Gly Ala Glu Met Glu Thr Asn Ile Thr Thr Cys Asn Ala Asp Gly Ser
        340                 345                 350

Val Thr Gly Ser Gly Ser Ser Cys Asp Asp Ile Pro Thr Ile Asp Leu
            355                 360                 365

Ile Pro Gln Tyr Leu Arg Phe Leu Gln Glu Trp Val Glu Asn Phe Cys
        370                 375                 380

Glu Gln Arg Gln Ala Lys Val Lys Asp Val Ile Thr Asn Cys Lys Ser
385                 390                 395                 400

Cys Lys Glu Ser Gly Asn Lys Cys Lys Thr Glu Cys Lys Thr Lys Cys
            405                 410                 415

Lys Asp Glu Cys Glu Lys Tyr Lys Lys Phe Ile Glu Ala Cys Gly Thr
        420                 425                 430

Ala Gly Gly Gly Ile Gly Thr Ala Gly Ser Pro Trp Ser Lys Arg Trp
            435                 440                 445

Asp Gln Ile Tyr Lys Arg Tyr Ser Lys His Ile Glu Asp Ala Lys Arg
        450                 455                 460

Asn Arg Lys Ala Gly Thr Lys Asn Cys Gly Thr Ser Ser Thr Thr Asn
465                 470                 475                 480

Ala Ala

<210> SEQ ID NO 4
<211> LENGTH: 1434
<212> TYPE: DNA
<213> ORGANISM: Plasmodium falciparum

<400> SEQUENCE: 4
ccttatttcg cagaatatgc aaccaaatta tcatttattt taaatccatc agatgctaat      60
aatccgtctg gagaaacagc aaaccataat gatgaagcat gtaactgtaa tgaatcagga     120
atttcatcag ttggacaggc acaaacatcg ggtccgtcgt cgaataaaac atgtatcaca     180
catagctcta taaaaactaa taagaaaaaa gaatgtaaag atgtaaagtt gggtgttcgt     240
gaaaatgata agatttgaa atatgcgta attgaggaca cttccttaag tggtgttgat     300
aattgttgtt gccaagattt attgggaatt cttcaagaaa attgtagtga taataaacgt     360
ggatctagtt ctaatgatag ttgtgataac aaaaatcagg atgaatgtca aagaaaatta     420
gaaaaagtat ttgcatcttt aacgaatggt tataaatgcg acaaatgtaa atctggaaca     480
tcaagaagta aaaaaaaatg gatatggaaa aaatcctctg gtaatgaaga aggattacaa     540
gaagaatatg ctaacaccat aggttacccc caagaacac aatcgttata tttaggaaat     600
ctacctaaac ttgaaaatgt gtgcgaagat gtaaggata ttaattttga tacaaaagag     660
aaatttctag caggatgctt aattgttct tttcatgaag gaaaaatttt aaaaaaaga     720

-continued

```
tacccctcaaa ataaaaattc tggaaataaa gaaaatttat gcaaagcttt agaatatagt    780
tttgctgatt atggagattt aattaaaggt acaagtatat gggataatga atatacaaaa    840
gatctggaac taaatttaca aaacaatttt ggaaaacttt ttggtaaata tataaaaaag    900
aataataccg ctgaacaaga tacttcatat tcttctcttg atgaattaag agaatcatgg    960
tggaacacga acaaaaaata tatttggaca gcaatgaaac atggtgcaga atgaatatt   1020 actacgtgta atgctgatgg tagtgtcact ggtagtggta gtagttgtga tgatattcct   1080
acgattgatt tgatcccgca atatttacgt tttttgcaag aatgggtaga aaatttttgc   1140
gaacaacgtc aagcaaaagt aaaagatgtg taacgaact gtaagtcgtg taaggaaagt   1200
ggaaacaaat gtaaactga atgtaaaaca aaatgtaaag acgagtgtga aaaatacaaa   1260
aaatttattg aagcgtgtgg tacagctggt ggtggtattg gtactgctgg atctccatgg   1320
agcaaaaggt gggaccaaat atataagagg tattccaaac atatagaaga cgcgaaacga   1380
aaccgtaaag cgggcacaaa aaattgtggt acaagtagta ctacaaatgc tgcc         1434
```

<210> SEQ ID NO 5
<211> LENGTH: 867
<212> TYPE: PRT
<213> ORGANISM: Plasmodium falciparum

<400> SEQUENCE: 5

```
Asn Lys Ile Glu Ala Tyr Leu Gly Ala Lys Ser Asp Asp Ser Lys Ile
1               5                   10                  15

Asp Gln Ser Leu Lys Ala Asp Pro Ser Glu Val Gln Tyr Tyr Gly Ser
            20                  25                  30

Gly Gly Asp Gly Tyr Tyr Leu Arg Lys Asn Ile Cys Lys Ile Thr Val
        35                  40                  45

Asn His Ser Asp Ser Gly Thr Asn Asp Pro Cys Asp Arg Ile Pro Pro
    50                  55                  60

Pro Tyr Gly Asp Asn Asp Gln Trp Lys Cys Ala Ile Ile Leu Ser Lys
65                  70                  75                  80

Val Ser Glu Lys Pro Glu Asn Val Phe Val Pro Arg Arg Gln Arg
            85                  90                  95

Met Glu Thr Cys Ile Asn Asn Leu Glu Lys Leu Asn Val Asp Lys Ile
            100                 105                 110

Arg Asp Lys His Ala Phe Leu Ala Asp Val Leu Leu Thr Ala Arg Asn
        115                 120                 125

Glu Gly Glu Arg Ile Val Gln Asn His Pro Asp Thr Asn Ser Ser Asn
    130                 135                 140

Val Cys Asn Ala Leu Glu Arg Ser Phe Ala Asp Ile Ala Asp Ile Ile
145                 150                 155                 160

Arg Gly Thr Asp Leu Trp Lys Gly Thr Asn Ser Asn Leu Glu Gln Asn
            165                 170                 175

Leu Lys Gln Met Glu Thr Phe Ala Lys Ile Arg Glu Asn Asp Lys Val
        180                 185                 190

Leu Gln Asp Lys Tyr Pro Lys Asp Gln Asn Tyr Arg Lys Leu Arg Glu
    195                 200                 205

Asp Trp Trp Asn Ala Asn Arg Gln Lys Val Trp Glu Val Ile Thr Cys
    210                 215                 220

Gly Ala Arg Ser Asn Asp Leu Leu Ile Lys Gly Trp Arg Thr Ser
225                 230                 235                 240

Gly Lys Ser Asn Gly Asp Asn Lys Leu Glu Leu Cys Arg Lys Cys Gly
            245                 250                 255
```

His Tyr Glu Glu Lys Val Pro Thr Lys Leu Asp Tyr Val Pro Gln Phe
                260                 265                 270

Leu Arg Trp Leu Thr Glu Trp Ile Glu Asp Phe Tyr Arg Glu Lys Gln
            275                 280                 285

Asn Leu Ile Asp Asp Met Glu Thr Glu Arg His Arg Glu Glu Cys Thr
        290                 295                 300

Ser Glu Asp His Lys Ser Lys Glu Gly Thr Ser Tyr Cys Ser Thr Cys
305                 310                 315                 320

Lys Asp Lys Cys Lys Tyr Cys Glu Cys Val Lys Lys Trp Lys Ser
                325                 330                 335

Glu Trp Glu Asn Gln Lys Asn Lys Tyr Thr Glu Leu Tyr Gln Gln Asn
            340                 345                 350

Lys Asn Glu Thr Ser Gln Lys Asn Thr Ser Arg Tyr Asp Asp Tyr Val
        355                 360                 365

Lys Asp Phe Phe Lys Lys Leu Glu Ala Asn Tyr Ser Ser Leu Glu Asn
        370                 375                 380

Tyr Ile Lys Gly Asp Pro Tyr Phe Ala Glu Tyr Ala Thr Lys Leu Ser
385                 390                 395                 400

Phe Ile Leu Asn Ser Ser Asp Ala Asn Asn Pro Ser Glu Lys Ile Gln
            405                 410                 415

Lys Asn Asn Asp Glu Val Cys Asn Cys Asn Glu Ser Gly Ile Ala Ser
            420                 425                 430

Val Glu Gln Glu Gln Ile Ser Asp Pro Ser Ser Asn Lys Thr Cys Ile
            435                 440                 445

Thr His Ser Ser Ile Lys Ala Asn Lys Lys Val Cys Lys His Val
        450                 455                 460

Lys Leu Gly Val Arg Glu Asn Asp Lys Asp Leu Arg Val Cys Val Ile
465                 470                 475                 480

Glu His Thr Ser Leu Ser Gly Val Glu Asn Cys Cys Cys Gln Asp Phe
            485                 490                 495

Leu Arg Ile Leu Gln Glu Asn Cys Ser Asp Asn Lys Ser Gly Ser Ser
            500                 505                 510

Ser Asn Gly Ser Cys Asn Asn Lys Asn Gln Glu Ala Cys Glu Lys Asn
        515                 520                 525

Leu Glu Lys Val Leu Ala Ser Leu Thr Asn Cys Tyr Lys Cys Asp Lys
        530                 535                 540

Cys Lys Ser Glu Gln Ser Lys Lys Asn Asn Lys Asn Trp Ile Trp Lys
545                 550                 555                 560

Lys Ser Ser Gly Lys Glu Gly Gly Leu Gln Lys Glu Tyr Ala Asn Thr
            565                 570                 575

Ile Gly Leu Pro Pro Arg Thr Gln Ser Leu Cys Leu Val Val Cys Leu
            580                 585                 590

Asp Glu Lys Gly Lys Lys Thr Gln Glu Leu Lys Asn Ile Arg Thr Asn
            595                 600                 605

Ser Glu Leu Leu Lys Glu Trp Ile Ile Ala Ala Phe His Glu Gly Lys
        610                 615                 620

Asn Leu Lys Pro Ser His Glu Lys Asn Asp Asp Asn Gly Lys Lys
625                 630                 635                 640

Leu Cys Lys Ala Leu Glu Tyr Ser Phe Ala Asp Tyr Gly Asp Leu Ile
            645                 650                 655

Lys Gly Thr Ser Ile Trp Asp Asn Glu Tyr Thr Lys Asp Leu Glu Leu
            660                 665                 670

```
Asn Leu Gln Lys Ile Phe Gly Lys Leu Phe Arg Lys Tyr Ile Lys Lys
            675                 680                 685

Asn Asn Thr Ala Glu Gln Asp Thr Ser Tyr Ser Leu Asp Glu Leu
    690                 695                 700

Arg Glu Ser Trp Trp Asn Thr Asn Lys Lys Tyr Ile Trp Leu Ala Met
705                 710                 715                 720

Glu Thr Lys His Gly Ala Gly Met Glu Thr Asn Ser Thr Thr Cys Cys
                725                 730                 735

Gly Asp Gly Ser Val Thr Gly Ser Gly Ser Ser Cys Asp Asp Ile Pro
            740                 745                 750

Thr Ile Asp Leu Ile Pro Gln Tyr Leu Arg Phe Leu Gln Glu Trp Val
            755                 760                 765

Glu His Phe Cys Lys Gln Arg Gln Glu Lys Val Lys Pro Val Ile Glu
        770                 775                 780

Asn Cys Lys Ser Cys Lys Glu Ser Gly Gly Thr Cys Asn Gly Glu Cys
785                 790                 795                 800

Lys Thr Glu Cys Lys Asn Lys Cys Glu Val Tyr Lys Lys Phe Ile Glu
                805                 810                 815

Asp Cys Lys Gly Gly Asp Gly Thr Ala Gly Ser Ser Trp Val Lys Arg
            820                 825                 830

Trp Asp Gln Ile Tyr Lys Arg Tyr Ser Lys Tyr Ile Glu Asp Ala Lys
            835                 840                 845

Arg Asn Arg Lys Ala Gly Thr Lys Asn Cys Gly Pro Ser Ser Thr Thr
        850                 855                 860

Asn Ala Ala
865

<210> SEQ ID NO 6
<211> LENGTH: 2573
<212> TYPE: DNA
<213> ORGANISM: Plasmodium falciparum

<400> SEQUENCE: 6
aacaaaattg aagcatattt aggtgcaaaa tccgatgatt ctaaaataga ccaatcgttg      60
aaagctgatc ctagtgaagt gcagtactat ggaagtggag gtgatggata ttacttaaga     120
aaaaatattt gcaaaattac cgtgaatcat tcagattctg aacaaatgaa tccttgtgat     180
agaataccac ctccttatgg cgataatgac caatggaaat gtgccataat tttatctaaa     240
gtaagtgaaa aacctgaaaa tgtatttgtt cctccgagaa gacaacgtat gtgcattaac     300
aatttagaaa aattaaatgt tgataaaatt agggataaac atgcattttt ggcagatgta     360
ttacttacgg ccagaaatga aggagaaaga atagtgcaaa tcatccagat acaaatagtt     420
ccaatgtttg taatgcatta gaaagaagtt ttgctgacat tgcagatatt attgaggta      480 cagatctatg gaaggtact aatagtaatt tagaacaaaa tttaaaacaa atgtttgcaa     540
aaatacgaga aaacgacaag gtacttcaag ataaatacc aaaggaccaa aattatagaa     600
aattacgaga agattggtgg aatgctaata gacaaaaggt gtgggaagtt attacttgtg     660
gtgcgcgaag taacgattta ctcataaaac gtggatggag aacatctgga aaatctaatg     720 agacaataa acttgaattg tgtcgcaaat gtggccatta tgaagaaaag gttcctacca     780
aattagatta tgtccctcaa ttcttaaggt ggttaacaga atggatagag gatttttata     840
gagagaagca aaatctgatc gatgacatgg agagacaccg tgaagagtgt acatcagagg     900
atcataaatc taagaaggt acatcatatt gtagtacctg taaagacaaa tgtaagaaat     960
```

```
attgtgaatg tgtgaagaaa tggaaatccg aatgggaaaa tcaaaaaaat aaatatacag    1020
aattatatca acaaaacaaa aacgaaactt cgcaaaaaaa tacatcaaga tatgatgatt    1080
atgttaaaga ttttttttaaa aaacttgaag ctaattattc gtctcttgaa aattatataa    1140
agggtgatcc ttatttcgca gaatatgcaa ccaaattatc atttatttta aattcatcag    1200
atgctaataa tccgtctgaa aaaatacaaa aaaataatga tgaagtatgt aactgtaatg    1260
aatcaggaat tgcatctgtt gaacaggaac aaatatcgga tccgtcgtcg aataaaacat    1320
gtatcacaca tagctccata aaagctaata agaaaaaagt atgtaaacat gtaaagttgg    1380
gtgttcgtga aaatgataaa gatttgagag tatgcgtaat tgagcacact tccttaagtg    1440
gtgttgaaaa ttgttgttgc caagatttct tgcgaattct tcaagaaaat tgtagtgata    1500
ataaaagtgg atctagttct aatggtagtt gtaataacaa aaatcaggaa gcatgtgaaa    1560
aaaatttaga aaaagtactt gcatctttaa ctaattgtta taaatgcgac aaatgtaaat    1620
ctgaacaatc aaaaaaaaat aacaaaaatt ggatatggaa aaaatcctct ggtaaggaag    1680
gtggattaca aaagaatat gctaatacaa taggtttacc cccaagaaca caatccttat    1740
gtttagtagt gtgtttagat gaaaaaggaa aaaaaacaca agaacttaag aatattagga    1800
ccaattcaga attattaaaa gagtggataa ttgctgcatt tcatgaagga aaaaatttaa    1860
aaccttccca tgaaaaaaaa aatgatgaca atggaaaaaa attatgcaaa gctttagaat    1920
acagttttgc cgattatgga gatttaatta aaggtacaag tatatgggat aatgaatata    1980
caaaagattt ggaactaaat ttacaaaaaa tttttggaaa acttttttcgt aaatatataa    2040 aaaagaataa tactgctgaa caagatactt catattcttc tcttgatgaa ttaagagaat    2100
catggtggaa cacgaacaaa aaatatattt ggttagcaat gaaacatggt gcgggaatga    2160
atagtactac gtgttgtggt gatggtagtg tcactggtag tggtagtagt tgtgatgata    2220
ttcctacgat tgatttgatc cctcaatatt tacggttttt gcaagaatgg gtagaacatt    2280
tttgtaaaca acgtcaagaa aaagtaaaac ctgtgataga gaattgtaag tcgtgtaagg    2340
aaagtggagg tacatgtaac ggtgagtgta aaactgaatg taaaaataaa tgtgaagtat    2400
acaaaaaatt tattgaagac tgtaagggtg gtgatggtac tgctggatcc tcatgggtga    2460
aaaggtggga ccaaatatat aagaggtatt ccaaatatat agaagacgcg aaacgaaacc    2520
gtaaagcggg cacaaaaaat tgtggcccaa gtagtactac aaatgctgcc taa    2573
```

<210> SEQ ID NO 7
<211> LENGTH: 478
<212> TYPE: PRT
<213> ORGANISM: Plasmodium falciparum

<400> SEQUENCE: 7

```
Pro Tyr Phe Ala Glu Tyr Ala Thr Lys Leu Ser Phe Ile Leu Asn Ser
1               5                   10                  15

Ser Asp Ala Asn Asn Pro Ser Glu Lys Ile Gln Lys Asn Asn Asp Glu
            20                  25                  30

Val Cys Asn Cys Asn Glu Ser Gly Ile Ala Ser Val Glu Gln Glu Gln
        35                  40                  45

Ile Ser Asp Pro Ser Ser Asn Lys Thr Cys Ile Thr His Ser Ser Ile
    50                  55                  60

Lys Ala Asn Lys Lys Val Cys Lys His Val Lys Leu Gly Val Arg
65                  70                  75                  80

Glu Asn Asp Lys Asp Leu Arg Val Cys Val Ile Glu His Thr Ser Leu
                85                  90                  95
```

Ser Gly Val Glu Asn Cys Cys Cys Gln Asp Phe Leu Arg Ile Leu Gln
            100                 105                 110

Glu Asn Cys Ser Asp Asn Lys Ser Gly Ser Ser Asn Gly Ser Cys
    115                 120                 125

Asn Asn Lys Asn Gln Glu Ala Cys Glu Lys Asn Leu Glu Lys Val Leu
130                 135                 140

Ala Ser Leu Thr Asn Cys Tyr Lys Cys Asp Lys Cys Lys Ser Glu Gln
145                 150                 155                 160

Ser Lys Lys Asn Asn Lys Asn Trp Ile Trp Lys Lys Ser Ser Gly Lys
                165                 170                 175

Glu Gly Gly Leu Gln Lys Glu Tyr Ala Asn Thr Ile Gly Leu Pro Pro
            180                 185                 190

Arg Thr Gln Ser Leu Cys Leu Val Val Cys Leu Asp Glu Lys Gly Lys
        195                 200                 205

Lys Thr Gln Glu Leu Lys Asn Ile Arg Thr Asn Ser Glu Leu Leu Lys
    210                 215                 220

Glu Trp Ile Ile Ala Ala Phe His Glu Gly Lys Asn Leu Lys Pro Ser
225                 230                 235                 240

His Glu Lys Lys Asn Asp Asp Asn Gly Lys Lys Leu Cys Lys Ala Leu
                245                 250                 255

Glu Tyr Ser Phe Ala Asp Tyr Gly Asp Leu Ile Lys Gly Thr Ser Ile
            260                 265                 270

Trp Asp Asn Glu Tyr Thr Lys Asp Leu Glu Leu Asn Leu Gln Lys Ile
        275                 280                 285

Phe Gly Lys Leu Phe Arg Lys Tyr Ile Lys Lys Asn Thr Ala Glu
    290                 295                 300

Gln Asp Thr Ser Tyr Ser Ser Leu Asp Glu Leu Arg Glu Ser Trp Trp
305                 310                 315                 320

Asn Thr Asn Lys Lys Tyr Ile Trp Leu Ala Met Glu Thr Lys His Gly
                325                 330                 335

Ala Gly Met Glu Thr Asn Ser Thr Thr Cys Cys Gly Asp Gly Ser Val
            340                 345                 350

Thr Gly Ser Gly Ser Ser Cys Asp Asp Ile Pro Thr Ile Asp Leu Ile
        355                 360                 365

Pro Gln Tyr Leu Arg Phe Leu Gln Glu Trp Val Glu His Phe Cys Lys
370                 375                 380

Gln Arg Gln Glu Lys Val Lys Pro Val Ile Glu Asn Cys Lys Ser Cys
385                 390                 395                 400

Lys Glu Ser Gly Gly Thr Cys Asn Gly Glu Cys Lys Thr Glu Cys Lys
                405                 410                 415

Asn Lys Cys Glu Val Tyr Lys Lys Phe Ile Glu Asp Cys Lys Gly Gly
            420                 425                 430

Asp Gly Thr Ala Gly Ser Ser Trp Val Lys Arg Trp Asp Gln Ile Tyr
        435                 440                 445

Lys Arg Tyr Ser Lys Tyr Ile Glu Asp Ala Lys Arg Asn Arg Lys Ala
    450                 455                 460

Gly Thr Lys Asn Cys Gly Pro Ser Ser Thr Thr Asn Ala Ala
465                 470                 475

<210> SEQ ID NO 8
<211> LENGTH: 1422
<212> TYPE: DNA
<213> ORGANISM: Plasmodium falciparum

<400> SEQUENCE: 8

```
ccttatttcg cagaatatgc aaccaaatta tcatttattt taaattcatc agatgctaat      60
aatccgtctg aaaaaataca aaaaaataat gatgaagtat gtaactgtaa tgaatcagga     120
attgcatctg ttgaacagga acaaatatcg gatccgtcgt cgaataaaac atgtatcaca     180
catagctcca taaaagctaa taagaaaaaa gtatgtaaac atgtaaagtt gggtgttcgt     240
gaaaatgata aagatttgag agtatgcgta attgagcaca cttccttaag tggtgttgaa     300
aattgttgtt gccaagattt cttgcgaatt cttcaagaaa attgtagtga taataaaagt     360
ggatctagtt ctaatggtag ttgtaataac aaaaatcagg aagcatgtga aaaaaattta     420
gaaaaagtac ttgcatcttt aactaattgt tataaatgcg acaaatgtaa atctgaacaa     480
tcaaaaaaaa ataacaaaaa ttggatatgg aaaaaatcct ctggtaagga aggtggatta     540
caaaagaat atgctaatac aataggttta cccccaagaa cacaatcctt atgtttagta      600
gtgtgtttag atgaaaaagg aaaaaaaaca caagaactta agaatattag gaccaattca     660
gaattattaa aagagtggat aattgctgca tttcatgaag gaaaaaattt aaaaccttcc     720
catgaaaaaa aaaatgatga caatggaaaa aaattatgca agctttaga atacagtttt      780
gccgattatg gagatttaat taaaggtaca agtatatggg ataatgaata tacaaaagat     840
ttggaactaa atttacaaaa aattttttgga aacttttttc gtaaatatat aaaaagaat     900
aatactgctg aacaagatac ttcatattct tctcttgatg aattaagaga atcatggtgg    960
aacacgaaca aaaatatat ttggttagca atgaaacatg gtgcgggaat gaatagtact    1020
acgtgttgtg gtgatggtag tgtcactggt agtggtagta gttgtgatga tattcctacg    1080
attgatttga tccctcaata tttacggttt ttgcaagaat gggtagaaca tttttgtaaa    1140
caacgtcaag aaaagtaaa acctgtgata gagaattgta agtcgtgtaa ggaaagtgga     1200
ggtacatgta acggtgagtg taaaactgaa tgtaaaaata aatgtgaagt atacaaaaaa    1260
tttattgaag actgtaaggg tggtgatggt actgctggat cctcatgggt gaaaggtgg     1320
gaccaaatat ataagaggta ttccaaatat atagaagacg cgaaacgaaa ccgtaaagcg    1380
ggcacaaaaa attgtggccc aagtagtact acaaatgctg cc                       1422
```

<210> SEQ ID NO 9
<211> LENGTH: 17
<212> TYPE: DNA
<213> ORGANISM: Artificial Sequence
<220> FEATURE:
<223> OTHER INFORMATION: sense primer

<400> SEQUENCE: 9

```
ttayccccaa gaacaca                                                    17
```

<210> SEQ ID NO 10
<211> LENGTH: 20
<212> TYPE: DNA
<213> ORGANISM: Artificial Sequence
<220> FEATURE:
<223> OTHER INFORMATION: antisense primer

<400> SEQUENCE: 10

```
ttttaaattt tttccatgaa                                                 20
```

<210> SEQ ID NO 11
<211> LENGTH: 181
<212> TYPE: PRT
<213> ORGANISM: Artificial Sequence

```
<220> FEATURE:
<223> OTHER INFORMATION: new cluster consensus sequence
<220> FEATURE:
<221> NAME/KEY: MISC_FEATURE
<222> LOCATION: (3)..(3)
<223> OTHER INFORMATION: Xaa is Ile or Val
<220> FEATURE:
<221> NAME/KEY: MISC_FEATURE
<222> LOCATION: (5)..(5)
<223> OTHER INFORMATION: Xaa is any amino acid or is absent
<220> FEATURE:
<221> NAME/KEY: MISC_FEATURE
<222> LOCATION: (6)..(6)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (10)..(10)
<223> OTHER INFORMATION: Xaa is any amino acid or is absent
<220> FEATURE:
<221> NAME/KEY: MISC_FEATURE
<222> LOCATION: (30)..(30)
<223> OTHER INFORMATION: Xaa is any amino acid or is absent
<220> FEATURE:
<221> NAME/KEY: MISC_FEATURE
<222> LOCATION: (47)..(47)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (53)..(53)
<223> OTHER INFORMATION: Xaa is any amino acid or is absent
<220> FEATURE:
<221> NAME/KEY: MISC_FEATURE
<222> LOCATION: (62)..(62)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (65)..(65)
<223> OTHER INFORMATION: Xaa is Ile or Val
<220> FEATURE:
<221> NAME/KEY: MISC_FEATURE
<222> LOCATION: (66)..(66)
<223> OTHER INFORMATION: Xaa is any amino acid or is absent
<220> FEATURE:
<221> NAME/KEY: MISC_FEATURE
<222> LOCATION: (96)..(96)
<223> OTHER INFORMATION: Xaa is any amino acid or is absent
<220> FEATURE:
<221> NAME/KEY: MISC_FEATURE
<222> LOCATION: (97)..(97)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (104)..(105)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (112)..(112)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (117)..(117)
<223> OTHER INFORMATION: Xaa is any amino acid or is absent
<220> FEATURE:
<221> NAME/KEY: MISC_FEATURE
<222> LOCATION: (120)..(120)
<223> OTHER INFORMATION: Xaa is any amino acid or is absent
<220> FEATURE:
<221> NAME/KEY: MISC_FEATURE
<222> LOCATION: (127)..(127)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (145)..(145)
<223> OTHER INFORMATION: Xaa is Ile or Val
<220> FEATURE:
<221> NAME/KEY: MISC_FEATURE
<222> LOCATION: (162)..(162)
<223> OTHER INFORMATION: Xaa is any amino acid or is absent
```

```
<220> FEATURE:
<221> NAME/KEY: MISC_FEATURE
<222> LOCATION: (163)..(163)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (174)..(175)
<223> OTHER INFORMATION: Xaa is any amino acid or is absent

<400> SEQUENCE: 11

Asp Tyr Xaa Lys Xaa Xaa Pro Tyr Ser Xaa Glu Tyr Gly Lys Leu Leu
1               5                   10                  15

Lys Phe Asp Asn Thr Asn Ala Phe Lys Glu Ser Ile Thr Xaa Asn Lys
            20                  25                  30

Asn Val Cys Ser Cys Ser Gly Asn Glu Lys Leu Ile Ile Ser Xaa Gly
        35                  40                  45

Ser Ser Ser Xaa Ser Phe Gly Thr Ser Phe Ser Tyr Xaa Asn Ser
    50                  55                  60

Xaa Xaa Thr Ser Asn Lys Arg Lys Glu Cys Lys Gln Ile Lys Phe Ser
65                  70                  75                  80

Gly Asn Lys Asn Asn Met Asn Ile Asn Ile Cys Ser Thr Gln Asp Xaa
                85                  90                  95

Xaa Asn Leu Leu Val Lys Leu Xaa Xaa Leu Leu Lys Gly Phe Cys Xaa
            100                 105                 110

Thr Cys Asp Thr Xaa Ile Gly Xaa Val Glu Val Val Ser Glu Xaa Asn
            115                 120                 125

Cys Glu Glu Gln Tyr Lys Lys Leu Leu Pro Cys Leu Glu Lys Cys Thr
130                 135                 140

Xaa Leu Asn Cys Asn Glu Cys Asn Lys Thr Arg Cys Lys Pro Leu Lys
145                 150                 155                 160

Lys Xaa Xaa Glu Lys Trp Ile Trp Gly Lys Pro Lys Gln Xaa Xaa Ala
            165                 170                 175

Gly Leu Gln Lys Glu
            180

<210> SEQ ID NO 12
<211> LENGTH: 190
<212> TYPE: PRT
<213> ORGANISM: Artificial Sequence
<220> FEATURE:
<223> OTHER INFORMATION: consensus sequence for cluster comprising the
      FCR3 and 3D7 lines
<220> FEATURE:
<221> NAME/KEY: MISC_FEATURE
<222> LOCATION: (1)..(1)
<223> OTHER INFORMATION: Xaa is any amino acid or is absent
<220> FEATURE:
<221> NAME/KEY: MISC_FEATURE
<222> LOCATION: (3)..(3)
<223> OTHER INFORMATION: Xaa is Ile or Val
<220> FEATURE:
<221> NAME/KEY: MISC_FEATURE
<222> LOCATION: (13)..(13)
<223> OTHER INFORMATION: Xaa is any amino acid or is absent
<220> FEATURE:
<221> NAME/KEY: MISC_FEATURE
<222> LOCATION: (26)..(26)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (33)..(33)
<223> OTHER INFORMATION: Xaa is any amino acid or is absent
<220> FEATURE:
<221> NAME/KEY: MISC_FEATURE
<222> LOCATION: (57)..(57)
<223> OTHER INFORMATION: Xaa is any amino acid or is absent
```

```
<220> FEATURE:
<221> NAME/KEY: MISC_FEATURE
<222> LOCATION: (61)..(61)
<223> OTHER INFORMATION: Xaa is Asn, Asp, Gln, Glu, Asp/Asn, or Gln/Glu
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: MISC_FEATURE
<222> LOCATION: (85)..(85)
<223> OTHER INFORMATION: Xaa is Ile or Val
<220> FEATURE:
<221> NAME/KEY: MISC_FEATURE
<222> LOCATION: (87)..(87)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (94)..(94)
<223> OTHER INFORMATION: Xaa is Ile or Val
<220> FEATURE:
<221> NAME/KEY: MISC_FEATURE
<222> LOCATION: (106)..(106)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (124)..(124)
<223> OTHER INFORMATION: Xaa is any amino acid or is absent
<220> FEATURE:
<221> NAME/KEY: MISC_FEATURE
<222> LOCATION: (136)..(136)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (140)..(141)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (142)..(142)
<223> OTHER INFORMATION: Xaa is any amino acid or is absent
<220> FEATURE:
<221> NAME/KEY: MISC_FEATURE
<222> LOCATION: (144)..(144)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (148)..(148)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (161)..(161)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (161)..(161)
<223> OTHER INFORMATION: Xaa is Asn, Asp, Gln, Glu, Asp/Asn, or Gln/Glu
<220> FEATURE:
<221> NAME/KEY: MISC_FEATURE
<222> LOCATION: (173)..(174)
<223> OTHER INFORMATION: Xaa is any amino acid or is absent
<220> FEATURE:
<221> NAME/KEY: MISC_FEATURE
<222> LOCATION: (180)..(180)
<223> OTHER INFORMATION: Xaa is any amino acid or is absent
<220> FEATURE:
<221> NAME/KEY: MISC_FEATURE
<222> LOCATION: (185)..(185)
<223> OTHER INFORMATION: Xaa is any amino acid or is absent

<400> SEQUENCE: 12

Xaa Tyr Xaa Lys Asp Asp Pro Tyr Ser Ala Glu Tyr Xaa Thr Lys Leu
1               5                   10                  15

Ser Phe Ile Leu Asn Ser Ser Asp Ala Xaa Thr Ser Ser Glu Lys Ile
            20                  25                  30

Xaa Lys Asn Asn Asp Glu Val Cys Asn Cys Asn Glu Ser Glu Ile Ser
        35                  40                  45
```

```
Ser Val Gly Gln Ala Gln Thr Ser Xaa Pro Ser Ser Xaa Lys Thr Cys
    50                  55                  60

Ile Thr Xaa Ser Ser Ile Lys Ala Asn Lys Lys Val Cys Lys Asp
 65              70                  75                  80

Val Lys Leu Gly Xaa Arg Xaa Asn Asp Lys Asp Leu Lys Xaa Cys Val
                85                  90                  95

Ile Glu Asp Thr Ser Leu Ser Gly Val Xaa Asn Cys Cys Gln Asp
                100                 105                 110

Leu Leu Gly Ile Leu Gln Glu Asn Cys Ser Asp Xaa Asn Lys Ser Gly
            115                 120                 125

Ser Ser Ser Asn Gly Ser Cys Xaa Asn Lys Asn Xaa Xaa Xaa Cys Xaa
    130                 135                 140

Lys Asn Leu Xaa Lys Val Leu Ala Ser Leu Thr Asn Gly Tyr Lys Cys
145                 150                 155                 160

Xaa Lys Cys Lys Ser Glu Gln Ser Lys Lys Asn Asn Xaa Xaa Trp Ile
                165                 170                 175

Trp Lys Lys Xaa Ser Gly Asn Glu Xaa Gly Leu Gln Lys Glu
            180                 185                 190

<210> SEQ ID NO 13
<211> LENGTH: 543
<212> TYPE: DNA
<213> ORGANISM: Artificial Sequence
<220> FEATURE:
<223> OTHER INFORMATION: new cluster consensus nucleoide sequence
<220> FEATURE:
<221> NAME/KEY: misc_feature
<222> LOCATION: (28)..(28)
<223> OTHER INFORMATION: n is a, t, c, g or is absent
<220> FEATURE:
<221> NAME/KEY: misc_feature
<222> LOCATION: (89)..(89)
<223> OTHER INFORMATION: n is a, t, c, g or is absent
<220> FEATURE:
<221> NAME/KEY: misc_feature
<222> LOCATION: (157)..(157)
<223> OTHER INFORMATION: n is a, t, c, g or is absent
<220> FEATURE:
<221> NAME/KEY: misc_feature
<222> LOCATION: (197)..(199)
<223> OTHER INFORMATION: n is a, t, c, g or is absent
<220> FEATURE:
<221> NAME/KEY: misc_feature
<222> LOCATION: (275)..(275)
<223> OTHER INFORMATION: n is a, t, c, g or is absent
<220> FEATURE:
<221> NAME/KEY: misc_feature
<222> LOCATION: (287)..(288)
<223> OTHER INFORMATION: n is a, t, c, g or is absent
<220> FEATURE:
<221> NAME/KEY: misc_feature
<222> LOCATION: (359)..(361)
<223> OTHER INFORMATION: n is a, t, c, g or is absent
<220> FEATURE:
<221> NAME/KEY: misc_feature
<222> LOCATION: (359)..(361)
<223> OTHER INFORMATION: n is a, t, c, g or is absent

<400> SEQUENCE: 13
gattatataa aggatgatcc ttattccnca gaatatggaa aactattaaa atttgataac     60
actaatgcat ttaaagaatc tataacatnt aacaaaaatg tatgttcttg tagtggtaat    120 gaaaattga tcatatcaga aggatcatca agttcangtt cttttggaac atcgtttct     180 tatgaaaata gtgtaannc atcaaataag agaaaagaat gtaaacaaat aaaatttagt    240
```

```
ggtaataaaa ataatatgaa tattaatata tgttnccacg caggatnnaa caatttgttg    300
gtaaaattag aggagttatt gaaaggtttt tgcgatacat gtgacactga tattggagnn    360
nttgaggtag ttagtgagaa taattgcgaa gagcaatata aaaaactgct ccactgtctt    420
gagaaatgca ctgttttgaa ttgtaatgaa tgcaataaaa ctcgatgtaa accattaaaa    480
aaggaacaag aaaaatggat ttggggtaaa ccaaaacaag aagctgcagg gttgcaaaaa    540
gaa                                                                 543
```

<210> SEQ ID NO 14
<211> LENGTH: 570
<212> TYPE: DNA
<213> ORGANISM: Artificial Sequence
<220> FEATURE:
<223> OTHER INFORMATION: consensus nucleotide sequence for cluster
      comprising the FCR3 and 3D7 lines
<220> FEATURE:
<221> NAME/KEY: misc_feature
<222> LOCATION: (97)..(97)
<223> OTHER INFORMATION: n is a, t, c, g or is absent
<220> FEATURE:
<221> NAME/KEY: misc_feature
<222> LOCATION: (375)..(375)
<223> OTHER INFORMATION: n is a, t, c, g or is absent
<220> FEATURE:
<221> NAME/KEY: misc_feature
<222> LOCATION: (377)..(377)
<223> OTHER INFORMATION: n is a, t, c, g or is absent
<220> FEATURE:
<221> NAME/KEY: misc_feature
<222> LOCATION: (379)..(379)
<223> OTHER INFORMATION: n is a, t, c, g or is absent
<220> FEATURE:
<221> NAME/KEY: misc_feature
<222> LOCATION: (425)..(425)
<223> OTHER INFORMATION: n is a, t, c, g or is absent
<220> FEATURE:
<221> NAME/KEY: misc_feature
<222> LOCATION: (506)..(506)
<223> OTHER INFORMATION: n is a, t, c, g or is absent
<220> FEATURE:
<221> NAME/KEY: misc_feature
<222> LOCATION: (509)..(512)
<223> OTHER INFORMATION: n is a, t, c, g or is absent
<220> FEATURE:
<221> NAME/KEY: misc_feature
<222> LOCATION: (539)..(539)
<223> OTHER INFORMATION: n is a, t, c, g or is absent

<400> SEQUENCE: 14

```
aattatataa aggatgatcc ttattccgca gaatatgcaa ctaaattatc atttatttta     60
aattcatcag atgctaatac ttcgtctgaa aaaatanaaa aaaataatga tgaagtatgt    120
aactgtaatg aatcagaaat ttcatctgtt ggacaggcac aaacatcggg tccgtcgtcg    180
aataaaacat gtatcacaca tagctccata aaagctaata agaaaaaagt atgtaaagat    240
gtaaagttgg gtgttcgtga aaatgataaa gatttgaaaa tatgcgtaat tgaggacact    300
tccttaagtg gtgttgaaaa ttgttgttgc caagatttat tgggaattct tcaagaaaat    360
tgtagtgata ataancnang tggatctagt tctaatggta gttgtgataa caaaaatcag    420
gaagnatgtg aaaaaaattt agaaaaagta cttgcatctt taactaatgg ttataaatgc    480
gacaaatgta aatctggaac atcaanaann nntaacaaaa aatggatatg gaaaaaatnc    540
tctggtaatg aagaaggatt acaaaaagaa                                    570
```